(12) United States Patent
Yoo et al.

(10) Patent No.: US 11,432,685 B2
(45) Date of Patent: Sep. 6, 2022

(54) LEG CARE APPARATUS

(71) Applicant: LG ELECTRONICS INC., Seoul (KR)

(72) Inventors: Hyunsun Yoo, Seoul (KR); Jaehung Chun, Seoul (KR); Joogyeom Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 50 days.

(21) Appl. No.: 16/844,649

(22) Filed: Apr. 9, 2020

(65) Prior Publication Data

US 2021/0022566 A1 Jan. 28, 2021

(30) Foreign Application Priority Data

Jul. 24, 2019 (KR) .................. 10-2019-0089651
Jul. 24, 2019 (KR) .................. 10-2019-0089725

(51) Int. Cl.
| | | |
|---|---|---|
| *A47K 3/022* | (2006.01) | |
| *A61H 33/06* | (2006.01) | |
| *A61H 35/00* | (2006.01) | |
| *A61M 11/00* | (2006.01) | |

(52) U.S. Cl.
CPC ............ *A47K 3/022* (2013.01); *A61H 33/06* (2013.01); *A61H 35/00* (2013.01); *A61H 35/006* (2013.01); *A61M 11/005* (2013.01); *A61H 2033/068* (2013.01); *A61H 2201/0107* (2013.01); *A61H 2201/0192* (2013.01); *A61H 2205/102* (2013.01); *A61H 2205/106* (2013.01); *A61H 2205/108* (2013.01); *A61M 2210/086* (2013.01)

(58) Field of Classification Search
CPC ........ A47K 3/022; A61H 33/06; A61H 35/00; A61H 35/006; A61M 11/005
USPC .............................................. 4/622
See application file for complete search history.

(56) References Cited

U.S. PATENT DOCUMENTS

| | | | | |
|---|---|---|---|---|
| 3,760,800 | A * | 9/1973 | Staffin ..................... | A61H 33/04 601/17 |
| 3,832,740 | A * | 9/1974 | McClarrin ............. | A47K 3/022 4/611 |
| 4,192,297 | A * | 3/1980 | Labrecque ............... | A61H 9/00 601/166 |
| 4,620,529 | A * | 11/1986 | Kurosawa ............ | A61H 35/006 601/157 |
| 6,385,795 | B1 * | 5/2002 | Ferber .................... | A47K 3/022 4/622 |
| 2006/0026753 | A1 * | 2/2006 | Leung .................... | A61H 33/06 4/622 |
| 2006/0207016 | A1 * | 9/2006 | Lev .................... | A61H 15/0078 4/622 |

FOREIGN PATENT DOCUMENTS

| | | |
|---|---|---|
| CN | 205849771 U | 1/2017 |
| FR | 2760968 A1 | 9/1998 |

(Continued)

*Primary Examiner* — Huyen D Le
(74) *Attorney, Agent, or Firm* — Dentons US LLP

(57) ABSTRACT

A leg care apparatus includes a main body configured to provide an action space in which a leg is accommodated, a bottom module which is placed on a bottom surface of the main body and in which a component for a foot bath is accommodated, and an action space adjustment module configured to adjust a size of the action space.

17 Claims, 21 Drawing Sheets

(56) References Cited

FOREIGN PATENT DOCUMENTS

| | | | |
|---|---|---|---|
| GB | 2156218 | A | 10/1985 |
| KR | 1020110010331 | A | 2/2011 |
| KR | 2020110008207 | U | 8/2011 |
| KR | 10-2012-0031205 | A | 3/2012 |
| WO | 02074223 | A1 | 9/2002 |

\* cited by examiner

FIG. 16

```
SPRAY MIST              —S1
    ↓
ATTACH MIST TO LEG      —S2
    ↓
SUPPLY HEAT TO ACTION SPACE  —S3
```

LEG CARE APPARATUS

CROSS-REFERENCE TO RELATED APPLICATIONS

The present application claims priority under 35 U.S.C. 119 and 35 U.S.C. 365 to Korean Patent Application Nos. 10-2019-0089651 and 10-2019-0089725, all filed on Jul. 24, 2019, which are hereby incorporated by reference in their entirety.

BACKGROUND

The present disclosure relates to a leg care apparatus.

Foot bath is an action where user's feet are soaked in hot water for a predetermined time.

The foot bath is an action where heat is applied to the user's feet. In detail, the foot bath is known to be effective in improving various ailments such as blood circulation improvement, body temperature rise, improvement in feeling cold, improvement in sleep disorders, waste discharge, ingrown toenail prevention, plantar fasciitis improvement, stress relief, skin care, and the like by using heat transferred indirectly to the human body through the feet.

A device that provides hot water up to a height of the vicinity of an ankle to allow the user to soak their feet is widely known as a foot bath device that is capable of performing a foot bath. The foot bath device using water has limitations in that heat loss is large, the device is difficult to handle, and its use is troublesome because the feet have to be conduction-heated indirectly by heating water.

To solve these limitations, a foot bath device in which a heating element is provided inside a control space, and the foot bath is performed by using radiant heating using the heating element is being introduced. A foot bath machine using radiant heating is disclosed in Korean Patent registration No. 10-1145430.

The above-described device has the following limitations. First, there is inconvenience in that a user control panel is complicated to operate. Second, there is a limitation in that user's safety is threatened because a heating element is used. Third, there is a limitation in that the storage and movement of the device are difficult. Fourth, there is a limitation in that the device is frequently damaged due to having no rigidity. Fifth, it is troublesome to use because the control space is blocked by a plate. Sixth, there is a limitation in that only fomentation using the radiant heat is enabled in a radiant heating manner.

SUMMARY

Embodiments provide a leg care apparatus that includes a foot bath device to care a leg.

Embodiments also provide a leg care apparatus which is conveniently operated and used by a user.

Embodiments also provide a leg care apparatus in which a temperature control state is safely applied to a user's leg.

Embodiments also provide a leg care apparatus that is conveniently moved and stored.

Embodiments also provide a leg care apparatus that is prevented from being damaged due to rigidity and is easy to be handled by a user.

Embodiments also provide a leg care apparatus that is capable of enjoying a foot bath in various manners.

Embodiments also provide a leg care apparatus that is more conveniently moved and used by a user.

In one embodiment, a leg care apparatus includes: a main body configured to provide an action space in which a leg is accommodated; a bottom module which is placed on a bottom surface of the main body and in which a component for a foot bath is accommodated; and an action space adjustment module configured to adjust a size of the action space. Thus, foot bath may be adaptively and conveniently performed to be adapted to a user's leg, and the leg care apparatus may be conveniently performed by adjusting the leg care apparatus during movement and storage.

The action space adjustment module may include an upper module in which at least a portion of a top surface of the action space is defined and which opens and closes an inlet through which the leg is inserted into the action space. Thus, the user may effortlessly insert their leg into the leg care apparatus.

The upper module may be slidable vertically with respect to the main body, a vertical size of the leg care apparatus may be adjusted to provide the action space that is adapted to the user's leg, and the vertical size may be conveniently adjusted.

A knee care part configured to care a user's knee may be provided in the upper module to perform the knee care and the foot bath for the uncomfortable elderly people.

The action space adjustment module may include a side module in which at least a portion of a front surface of the action space is defined and which opens and closes the inlet through which the leg is inserted into the action space. Thus, when the user inserts the leg in the front and rear direction, the user's leg may be conveniently inserted. Particularly, the legs may be easily inserted into the action space without raising the legs highly.

The side module may be rotatable with respect to the main body so that the leg is conveniently inserted.

The side module may be supported on the bottom module to open the side module at a wider angle with respect to the bottom part.

A contact pad configured to conduct and transfer a temperature atmosphere by contacting a user's body may be provided in at least one of the main body, the action space adjustment module, and the bottom module. Thus, a heating atmosphere corresponding to the foot bath may be generated by conduction and transmission without using water.

The leg care apparatus may further include an atomizer configured to provide mist into the action space. Thus, the heat transfer by convection and conduction may be performed.

The atomizer may include at least one of an ultrasonic spray device or a heating spray device, and thus, the user may perform the foot bath by using water at an atmosphere desired by the user. For example, the foot bath in a hot atmosphere and the foot bath in a cold atmosphere in the general sense may be performed.

The leg care apparatus may further include a bottom supporter configured to allow movement of the leg care apparatus. According to an embodiment, the user may more conveniently move the leg care apparatus. Thus, the user may conveniently enjoy the foot bath at a desired place.

Two kinds of wheels having at least different sizes may be used as the bottom supporter, and thus, self-weight support and direction change may be performed by a separate structure. Thus, the wheel for adjusting the direction may be conveniently controlled.

A large wheel having a relatively large size among the two kinds of wheels may be installed at a rear portion of the bottom module to support a portion of the leg care apparatus, at which the self-weight is large.

The large wheel may be placed on each of both left and right sides of the bottom module to stably support the load of the leg care apparatus at both sides.

In another embodiment, a leg care apparatus includes: a main body configured to provide an action space in which a leg is accommodated; a bottom module placed on a bottom surface of the main body; and an upper module movably coupled to an upper portion of the main body or a side module movably coupled to a front portion of the main body so as to adjust an inlet, through which a user's leg is inserted. According to the embodiment, an upper module configured to adjust an inlet may be provided to flexibly respond to the user's body size and to allow the user to conveniently manipulate the leg care apparatus so that the leg is inserted.

In further another embodiment, a leg care apparatus includes: a main body configured to provide an action space in which a leg is accommodated; a bottom module provided below the main body to support the main body; and a bottom supporter configured to allow movement of the bottom module. According to the embodiment, the user more conveniently move the leg care apparatus. Thus, the user may conveniently enjoy the foot bath at a desired place.

Two kinds of wheels having at least different sizes may be used as the bottom supporter. Thus, the wheel for adjusting the direction may be conveniently controlled.

A movable wheel having a relatively small size among the two kinds of wheels may be installed at the front portion of the bottom module and is rotatable, and thus, the user may conveniently change a direction. Since the wheel is provided below the femoris at a front side to which force is applied, the direction of the leg care apparatus may be conveniently changed.

The movable wheel includes: a wheel; a wheel housing configured to support the wheel; and a rotation support shaft configured to vertically connect the wheel housing to the bottom module, the rotation support shaft being configured to allow rotation of the wheel housing in a left and right direction. Thus, the elderly may easily control the moving direction by easily operating the moving direction of the movable wheel.

The leg care apparatus may further include an elastic member configured to connect the wheel housing to the bottom module, the elastic member being configured to provide restoring force by which the wheel housing returns to an installation angle. Therefore, since the main directivity is given to the advancing direction, the elderly may also use the leg care apparatus more conveniently.

The details of one or more embodiments are set forth in the accompanying drawings and the description below. Other features will be apparent from the description and drawings, and from the claims.

BRIEF DESCRIPTION OF THE DRAWINGS

FIGS. 1 and 2 are front perspective views of a leg care apparatus according to an embodiment, wherein FIG. 1 illustrates a state in which the leg care apparatus is stored, and FIG. 2 illustrates a state in which the leg care apparatus is operated.

FIG. 16 is a flowchart for explaining a method for controlling a leg care apparatus according to an embodiment.

DETAILED DESCRIPTION OF THE EMBODIMENTS

Hereinafter, exemplary embodiments will be described in detail with reference to the accompanying drawings. The invention may, however, be embodied in many different forms and should not be construed as being limited to the embodiments set forth herein, and a person of ordinary skill in the art, who understands the spirit of the present invention, may readily implement other embodiments included within the scope of the same concept by adding, changing, deleting, and adding components. Thus, it should be understood that they are also included within the scope of the present invention.

Figure 1:
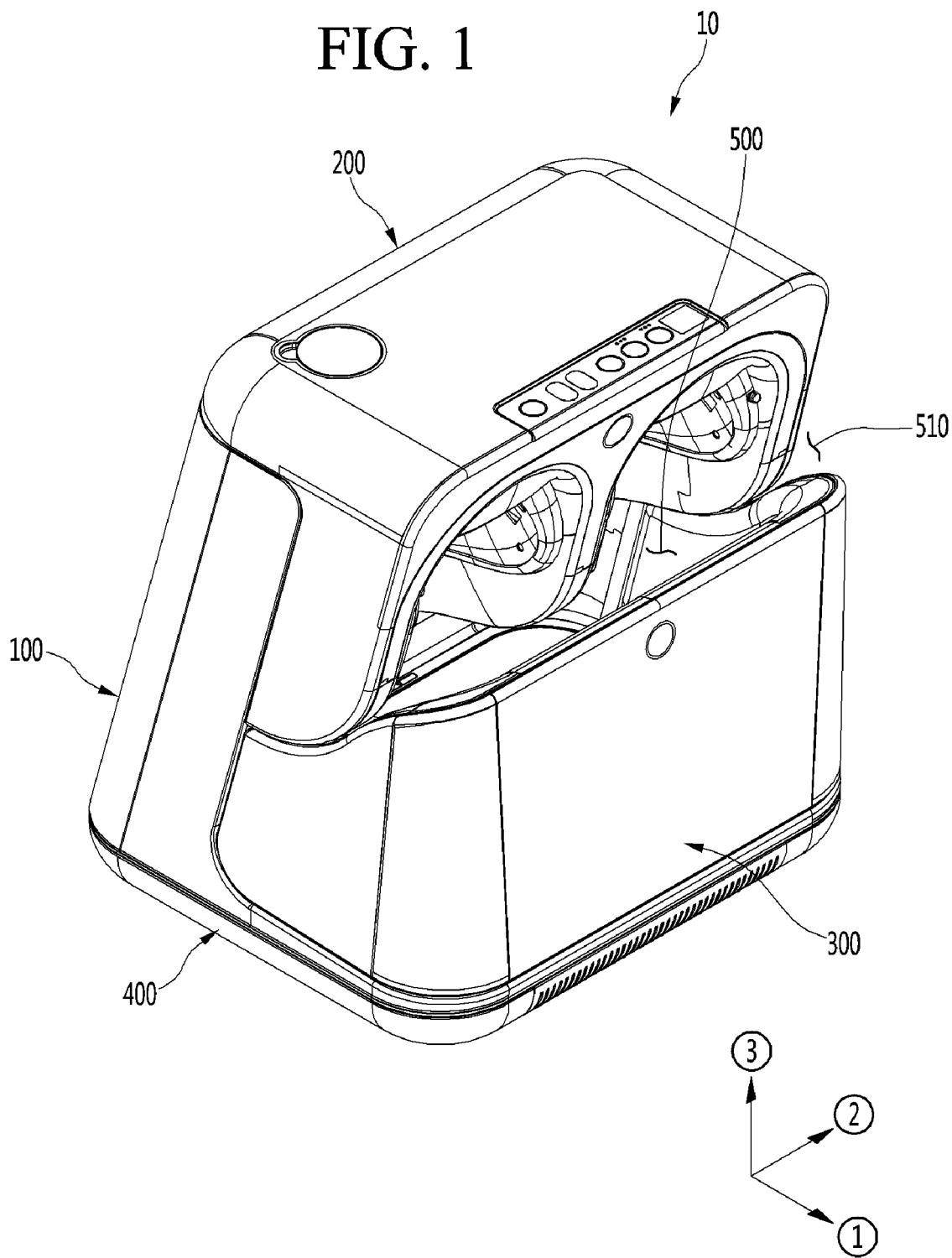
Figure 2:
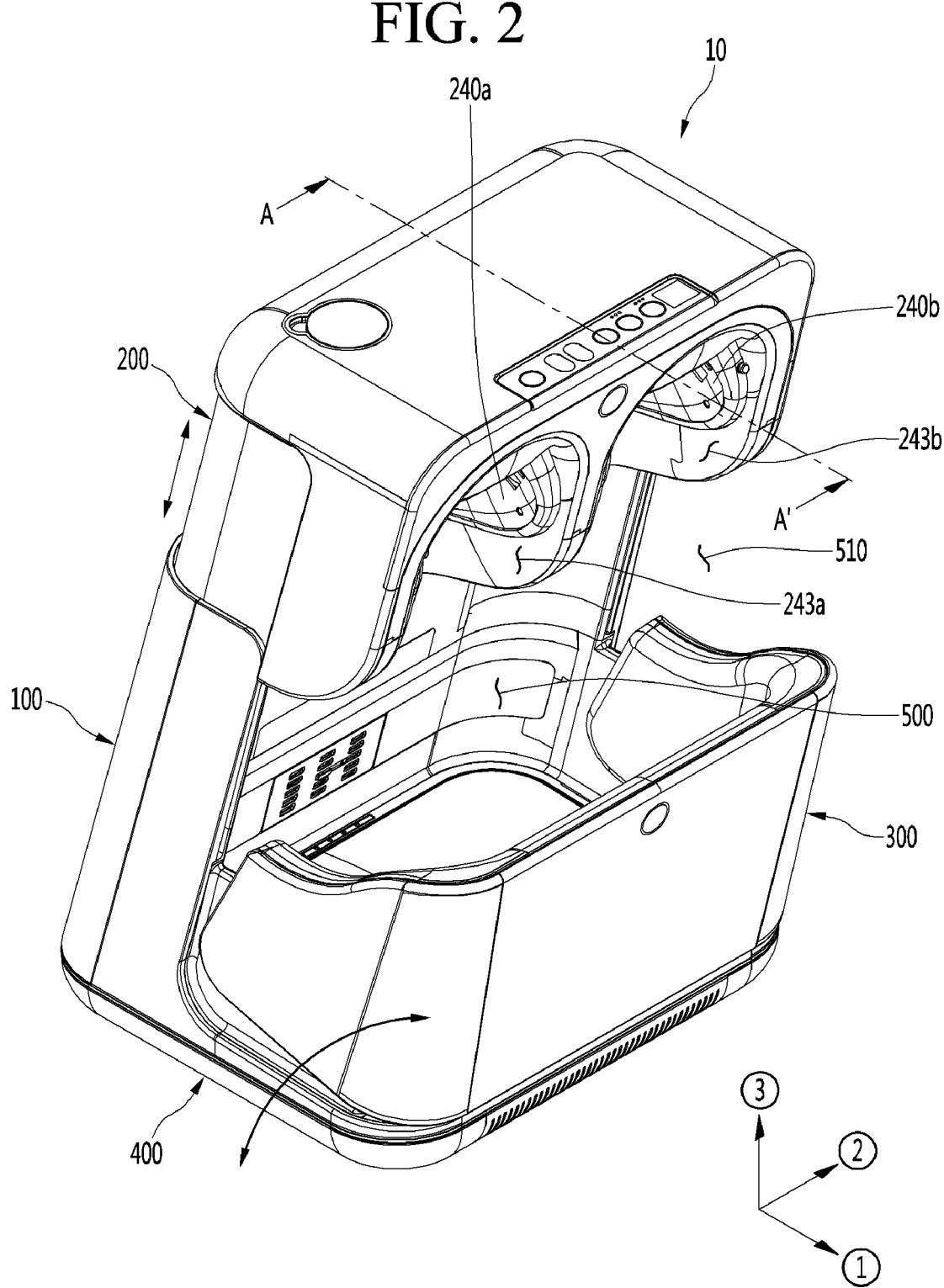

FIGS. 1 and 2 are front perspective views of a leg care apparatus according to an embodiment. That is, FIG. 1 illustrates a state in which the leg care apparatus is stored, and FIG. 2 illustrates a state in which the leg care apparatus is operated. Here, the storage state may mean a state in which the leg care apparatus has the smallest size or is not in use. The operation state may mean a state in which the leg care apparatus is expanded so that a user may insert their leg or a state in which the leg care apparatus is moved for use.

In the description of the drawings, a direction in which the user approaches indicates a front side. When based on each axis shown in the figures, the front and rear direction is expressed as ①, and the direction in which the user approaches indicates the front side. A left and right direction is expressed as ② and indicates a left and right direction of the front side with respect to the user. An upward and downward direction is expressed as ③ and indicates an upward and downward direction of the front side with respect to the user.

In the leg care apparatus according to an embodiment, in order to allow the user's leg to be inserted, an inlet may increase in size, and an inner action space may increase in volume. After the user's leg is inserted, the inlet may decrease in size to be suitable for the user's body, and the action space may decrease in volume to be suitable for the user's leg. Since the action space and the inlet are adjusted to be suitable for a body size of the user, particularly, a size and length of the leg, a thermal effect acting on the leg may be largely and quickly applied, and energy consumption may be saved.

According to an embodiment, the leg may be cared for by applying hot or cold air and/or pressure to a leg portion including portions of knees, calves, and thighs together with the feet.

In the following description, the meaning of the foot bath not only means foot bath using water pressure and heat applied in the water, but also applying heat, cold air, and pressure to a leg portion including portions of feet, knees, calves, and thighs.

Referring to FIGS. 1 and 2, a leg care apparatus 10 according to an embodiment includes a main body 100, an upper module 200 connected to an upper portion of the main body 100 to largely open an upper space of the leg care apparatus 10, a side module 300 connected to a front portion of the main body 100 to largely open an inner space of the leg care apparatus 10, and a bottom module 400 connected to a lower portion of the main body 100 to accommodate components that are required for operation of the leg care apparatus 10.

An action space 500 is provided in an inner space inside an inner surface of each of the main body 100, the upper module 200, the side module 300, and the bottom module 400. The action space 500 is a space for applying hot or cold air to a user's leg through at least one manner of conduction, convection, or radiation. An inlet 510 through which the user's leg is inserted and withdrawn is provided in front of the action space 500. Since at least one of the hot or cold air is applied to the user's leg in at least one manner of the conduction, convection, or radiation, the user may have a foot bath in a manner selected from various manners that are desired by the user.

The upper module 200 may perform a vertical elevation operation.

When the upper module 200 is moved upward, the inlet 510 is largely opened so that the user may conveniently insert their leg into the action space 500. After the user inserts their leg into the action space 500, the upper module 200 may be moved downward. The upper module 200 may be moved downward until a portion of the user's leg touches or the action space 500 is constructed in a shape desired by the user. The upper module 200 may define at least a portion of a top surface of the action space.

The upper module 200 is provided to be slid vertically in the embodiment, but is not limited thereto. For example, the upper module 200 may be opened through a rotation operation or moved to a position desired by the user.

Knee care parts 240a and 240b, each of which having a recessed shape, may be provided at both left and right side at the front of the upper module 200. Inner surfaces of the knee care parts may be provided with knee placing parts 243a and 243b. Each of the knee placing parts is a portion that contacts the user's knee. The knee placing part may include a light emitting element and a pad. The light emitting element and the pad may apply at least one of heat or pressure to care the knee, thereby performing blood flow improvement, muscle stimulation, and pain improvement.

The knee care part 240 cares the knee by applying at least one of the heat or the pressure. The action space 500 cares the user's leg through conduction, convection, and radiation of the hot or cold air. According to an embodiment, the leg care apparatus may improve user's satisfaction by performing a suitable action for each location of the leg. Particularly, the action space 500 may function as a foot bath machine by performing a function of the foot bath, and the knee care part 240 may function as a knee massager. The leg care apparatus according to embodiment may perform at least the functions of the foot bath machine and the knee massager.

The side module 300 may perform the rotation operation forward and backward.

When the side module 300 rotates forward, the inlet 510 may be opened so that the user may conveniently insert their leg into the action space 500. After the user inserts the leg into the action space, the side module 300 may rotate backward. The side module 300 may rotate backwards until a portion of the user's leg touches, or the action space 500 is constructed in a shape desired by the user. The side module 300 may provide at least a portion of a front surface of the action space.

The side module 300 rotates backward and forward in this embodiment, but the embodiment is not limited thereto. For example, the side module 300 may be slid to be opened or adjusted to a position desired by the user.

As described above, in the leg care apparatus 10 according to an embodiment, the upper module 200 and the side module 300 are contracted when not in use. Accordingly, the leg care apparatus 10 may be easily stored, moved, and handled in a state of being contracted in volume.

The upper module 200 and the side module 300 may be operable with respect to the main body 100. As a result, the action space may increase or decrease in volume. Thus, the functions such as the convenient handling, the foot bath that is suitable for the user, the leg contact, and the like may be performed. The upper module 200 and the side module 300 may perform the action of adjusting the size and shape of the action space. Thus, the upper module 200 and the side module 300 may be referred to as action space control modules.

Figure 3:
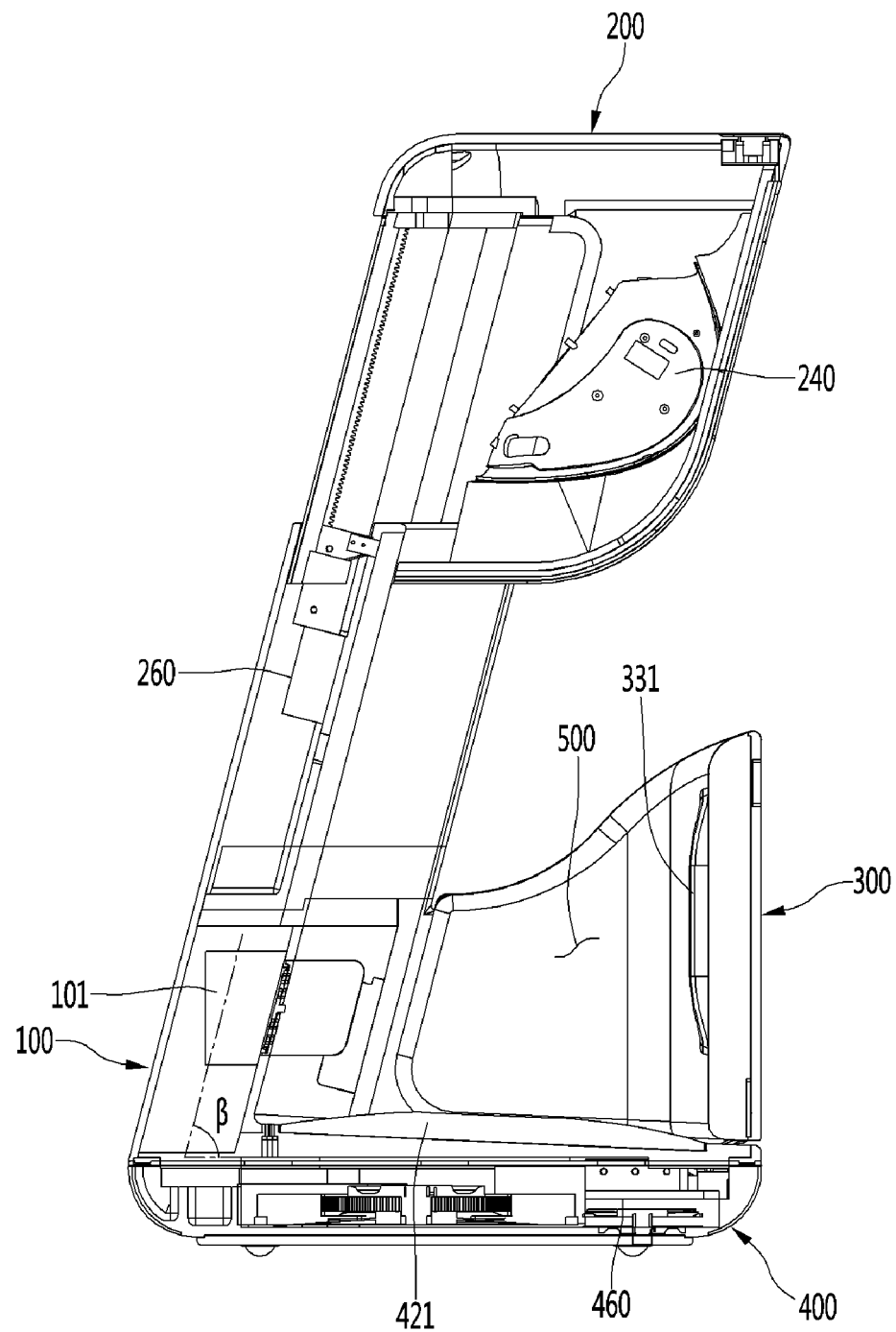
FIG. 3 is a schematic cross-sectional view taken along line A-A' of FIG. 2.

FIG. 3 is a schematic cross-sectional view taken along line A-A' of FIG. 2.

A schematic configuration and operation of the leg care apparatus according to an embodiment will be described with reference to FIG. 3. The main body 100 extends upward from a rear portion of the bottom module 400, and an upward extending angle is inclined forward at a predetermined angle β. Here, the inclined angle may be less than about 90 degrees as an acute angle. Since the main body 100 is inclined forward to extend, the user may not need to bend the knee excessively while inserting their leg into the action space 500 or while using the leg care apparatus.

Patients that need to care their leg by using the leg care apparatus may suffer from orthopedic diseases such as knee arthritis. The main body 100 may be provided to be inclined forward so that the action space 500 corresponds to a large bent angle of the user's leg without the patients having to excessively bend the knee. For example, the user may use the leg care apparatus even if the knee is not bent more than about 90 degrees.

Since a main vertical extension part (see reference numeral 111 of FIG. 5) of the main body 100 is provided to be inclined forward, other components related thereto may also be provided to be inclined.

The upper module 200 is provided on an upper portion of the main body 100. A vertical opening device 260 may be inserted into a contact part between the upper module 200 and the main body 100. The vertical opening device 260 may include a driving motor and a gear train and may move the upper module 200 upward or downward with respect to the main body 100.

The upper module 200 being moved upward may be when the inlet 510 is opened so that the user's leg is inserted into the action space 500. Alternatively, the upper module 200 may be moved upward even when the user withdraws their leg from the action space 500. The upper module 200 being moved downward may be when the inlet 510 decreases in size, or the action space is contracted after the user inserts their leg.

The knee care part 240 may be disposed on a front portion of the upper module 200 to care the user's knee.

A blower 101 may be provided below the main body 100. The blower 101 may provide hot air into the action space 500. The hot air of the blower 101 may be heated by a heating wire provided in the blower 101. The blower 101 may perform an action for forced convection of air heated by an external separate heating device.

The bottom module 400 may be disposed on a bottom part of the leg care apparatus to support the entire apparatus at a lower side. A foot contact pad 421 may be disposed on a top surface of the bottom module 400. A sole of the foot may contact the foot contact pad 421. The foot contact pad 421 may perform a foot bath function by conducting a temperature atmosphere controlled by an external force to the user's foot.

A front and rear opening device 460 may be disposed on a front portion of the bottom module 400. The front and rear opening device 460 may include a motor and a gear train and may be inserted into a contact part between the bottom module 400 and the side module 300. The front and rear opening device 460 may move the side module 300 forward and backward with respect to the main body 100.

A calf contact pad 331 may be disposed on an inner surface of the side module 300. A user's calf may contact the calf contact pad 331. The calf contact pad 331 may perform the foot bath function by conducting a temperature atmosphere controlled by an external force to the user's calf.

The side module 300 rotating forward may be when the inlet 510 is opened so that the user's leg is inserted into the action space 500. Alternatively, the side module 300 may be moved forward even when the user withdraws their leg from the action space 500. The side module 300 being moved backward may be when the inlet 510 decreases in size, and the action space is contracted, or the calf contacts the calf contact pad 331 after the user inserts their leg.

When the upper module 200 and the side module 300 open the inlet 510, the upper module 200 may start the opening thereof first, and then, the side module 300 may be opened. This is done because the upper module 200 performs the sliding operation, while the side module 300 rotates, and thus, if the side module 300 rotates forward first, the side module 300 may interfere with the upper module 200.

When the upper module 200 and the side module 300 close the inlet 510, the upper module 200 and the side module 300 may be operated in reverse. For example, the side module 300 may be closed first at a predetermined angle, and then the side module 300 may be closed. Since the respective modules are operated in this order, the interference between the modules may be prevented.

Figure 4:
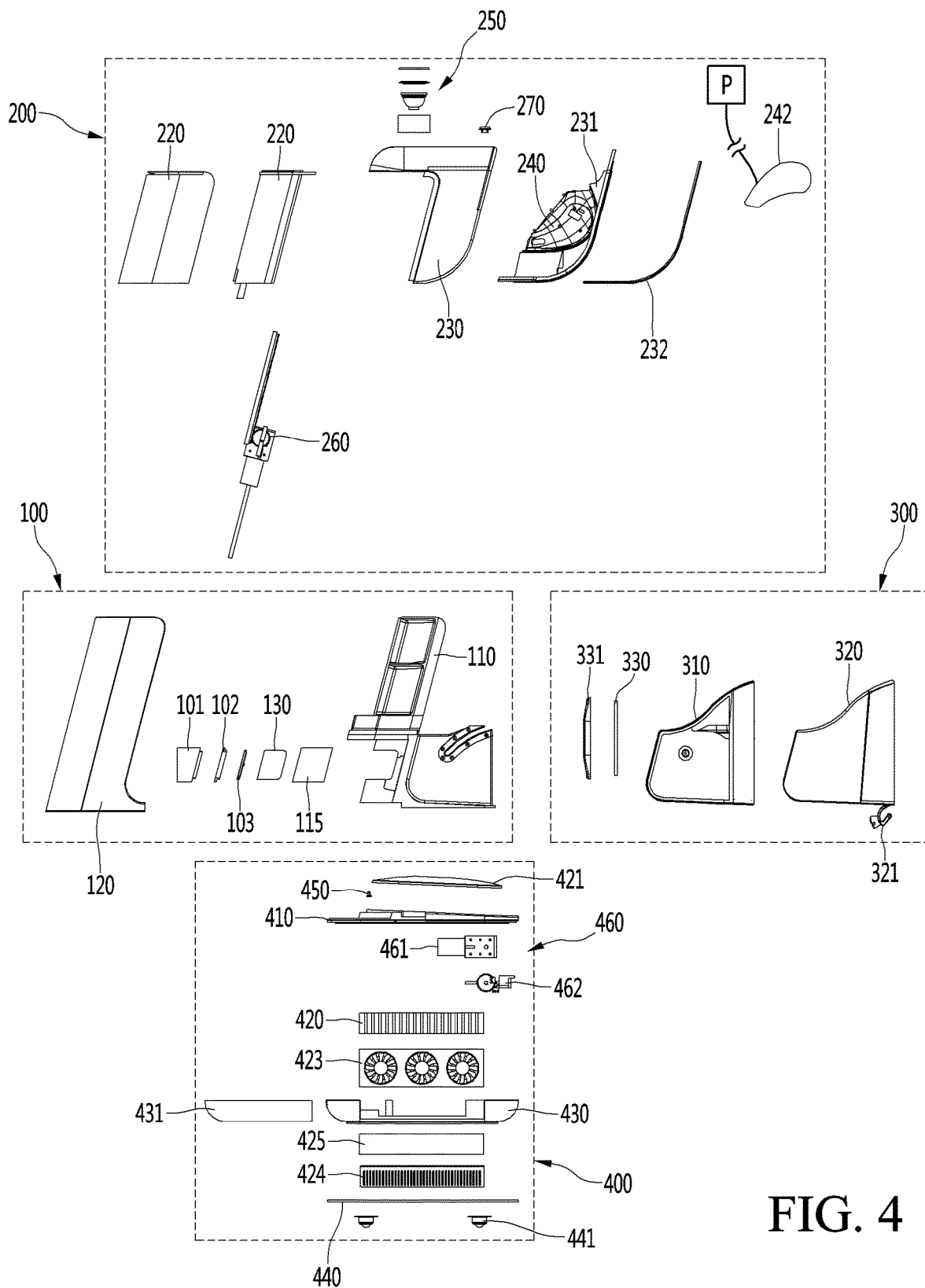
FIG. 4 is an exploded side view of the entire leg care apparatus according to an embodiment.

FIG. 4 is an exploded side view of the entire leg care apparatus according to an embodiment. Constituents of each module of the leg care apparatus according to the embodiment will be described with reference to FIG. 4.

First, the main body 100 is provided with a main frame 110 and a main body outer cover 120 provided on a rear surface of the main frame 110. A predetermined empty space may be provided between the main frame 110 and the main body outer cover 120, and components required for operating the leg care apparatus may be accommodated in the empty space.

The main body 100 may include a blower 101, a fragrance case 102 for accommodating a fragrance kit 103, and an atomizer 130. In addition, a heat generator, a radiant heater, and a cooler may be further provided.

The blower 101 is a device for generating a forced air current in the action space 500. The fragrance kit 103 may be provided as a device that provides fragrance into the action space 500 or remove a smell from the action space 500.

The atomizer 130 may supply mist to the inside of the action space 500 in at least one manner selected from ultrasonic spraying and heating spraying of water. A case in which both types of mist providing manners are installed may also be included in the embodiment.

The upper module 200 includes an upper frame 210 to which a portion of a movable member of the vertical opening device 260 is fixed to be elevated with respect to the main frame 100. An upper inner cover 230 and an upper outer cover 220 may be provided at an inner side and an outer side of the upper frame 210, respectively, to define an outer appearance of the upper module 200.

The knee care part 240, and a knee care seating panel 232 for mounting the knee care part 240 may be provided in front of the upper inner cover 230.

The side module 300 may include a side frame 310 and a side outer cover 320 provided in front of the side frame 310.

A calf thermoelectric module 330 and the calf contact pad 331 may be provided on an inner surface of the side module 300. A thermoelectric element may be provided in the calf thermoelectric module 330 to supply cold and hot air as desired by the user.

The bottom module 400 includes a bottom frame 410, a bottom housing 430 accommodating an outer edge of the bottom frame 410, and a bottom plate 440 that opens and closes a lower portion of the bottom frame 410.

A bottom supporter 441 provided as a wheel or the like is provided on a bottom surface of the bottom plate 440 so that the user may easily move the leg care apparatus.

The foot thermoelectric module 420 and the foot contact pad 421 that transfers the cold and hot air of the foot thermoelectric module 420 to the user's foot in a conduction manner may be provided inside the bottom housing 430. The foot thermoelectric module 420 and the foot contact pad 421 may contact each other to transfer heat. A heat exchange fan 423, a grill 424, and a filter 425 may be further provided as constituents for the hot or cold air that is exhausted from the foot thermoelectric module 420 to the outside.

The front and rear opening device 460 may be accommodated in the bottom housing 430 so that the side module 430 rotates. The front and rear opening device 460 may be provided with a rotation driving part 461 including at least a motor and a link driving part 462 including a power transmission part such as a gear.

The bottom housing 430 is provided with a light emitting element 450 that is exposed upward so that heat is irradiated to the user's foot. In this case, the light emitting element may irradiate infrared rays. The light emitting element 450 may be provided as an ultraviolet lamp to sterilize and disinfect the action space 500.

A water tray 431 that stores water to be discharged and through which the stored waste water is removed as necessary may be further provided at one side of the bottom housing 430. Water condensed after being atomized from the atomizer 130 to perform a predetermined function may be dropped into and stored in the water tray 431.

Hereinafter, each constituent of the leg care apparatus will be described in more detail.

Figure 5:
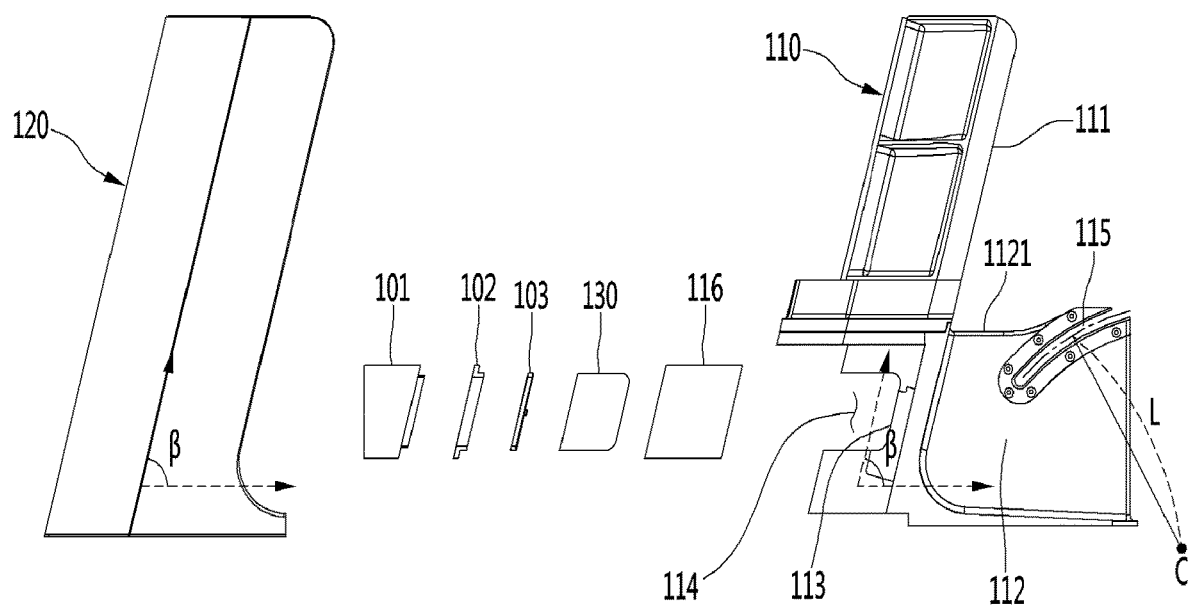
FIG. 5 is an exploded side view of a main body.

FIG. 5 is an exploded side view of the main body. A configuration and operation of the main body will be described in more detail with reference to FIGS. 4 and 5.

Referring to FIGS. 4 and 5, the main body 100 may be largely divided into a main frame 110 that defines an overall shape of the leg care apparatus and supports a load of the leg care apparatus, and a main body outer cover 120 providing a predetermined space for accommodating components between the main body outer cover 120 and the main frame 110 and disposed behind the main frame 110.

At least a portion of the upper module 200 may be inserted into an interval between the main frame 110 and the main body outer cover 120, and thus, the upper module 200 may be vertically movable in a state of being guided to the main body 100. For this, the vertical opening device 260 may be accommodated in the interval between the main frame 110 and the main body outer cover 120.

The main frame 110 may be provided with a main front and rear extension part 112 extending forward and backward from a lower portion thereof and a main vertical extension part 111 extending upward from a rear portion of the main front and rear extension part 112. The main vertical extension part 111 may extend forward in a state of being inclined at a predetermined angle β with respect to the main front and rear extension part 112. The predetermined angle may be an acute angle. Thus, the user may insert their leg into the action space 500 in a more comfortable posture and use the leg care apparatus.

The main front and rear extension part 112 may be provided to close both sides of the lower portion of the action space 500. Thus, the forced air current within the action space 500 may not be lost through both side surfaces of the action space 500.

A guide slot 115 that guides the rotation of the side module 300 may be provided in the main front and rear extension part 112. The guide slot 115 may be provided to open the main front and rear extension part 112 in a curved shape and also be provided to define a groove having a curved shape in the main front and rear extension part 112. A protrusion (see reference numeral 313 of FIG. 7) of the side module 300 may be placed to be guided within the guide slot 115.

To guide the protrusion 313, the guide slot 115 may be provided as a curve having a geometric center with respect to a predetermined rotation center point C. The guide slot 115 may be provided in a curved shape having a predetermined length L as a curvature radius at the rotational center point C. The rotation center point C may be one point of a movement support part (see reference numeral 321 of FIG. 7) of the side module 300.

The main front and rear extension part 112 is completely closed except for a region of the guide slot 115. The guide slot 115 may be completely covered by the side frame 310 of the side module 300. This is the same as in a case in which the side module 330 completely rotates forward to be opened. Thus, both spaces of the action space 500 may be completely covered, and the forced air, which is artificially manipulated, in the action space 500 may leak to the outside.

For this, the side frame 310 may accommodate the main front and rear extension part 112 therein. Also, a flow blocking film 1121 that blocks the air leakage of the action space may extend up to an upper end of the main front and rear extension part 112. The flow blocking film 1121 may block the action space 500 even when the side module 300 is opened to cover the inside of the action space 500 from the outside.

An operation of the flow blocking film 1121 may be seen in FIG. 2. FIG. 2 illustrates a state in which the flow blocking film 1121 is exposed to the outside of a side portion side surface part 311 to cover the action space 500 in a state in which the side module 300 is opened.

Referring to FIG. 5, a main rear surface part 113 having a rear opening 114 may be provided on a rear surface of the main front and rear extension part 112. Components that provide various atmospheres required for the operation of the action space 500 may be mounted at a rear side of the main rear surface part 113. An operation medium that provides an atmosphere of the action space 500, such as air, light, and mist may pass through the rear surface opening 114.

The components that are placed at the rear side of the main rear surface part 113 may include the blower 101 that performs a blowing operation, the fragrance kit 103 that cleanly maintains the action space, the fragrance case 102 in which the fragrance kit 103 is accommodated, and the atomizer 130 that provides mist. Alternatively, other components may be further provided for a smooth operation of the action space 500.

The blower 101 may suction air from at least one of the inside or the outside of the action space 500 to supply the air to the action space 500. Here, the air supplied into the action space 500 may be artificially controlled in temperature. To control the temperature, the blower 101 may be provided with a separate temperature controller that is exemplified as the heat generator and the cooler.

The blower 101 may suction air within the action space 500 to apply a predetermined artificial operation to the suctioned air, thereby supplying the air into the action space 500. This may be understood as an air circulation inside the action space 500. Accordingly, energy efficiency may be improved by reducing the operation medium disposed to the outside.

An example of the fragrance kit 103 may include perfume and a photocatalyst smell decomposition device. The perfume may be a component that supplies an artificially good smell. The photocatalyst smell decomposition device is a member that is exemplified as titanium oxide and may be a device for decomposing smell particles by a catalytic action using action light such as ultraviolet light.

The atomizer 130 is a device for supplying mist. When the atomizer 130 is operated in the ultrasonic spraying manner, the mist may be supplied to the inside of the action space 500 without being hot, the legs may be cared while being cool, and the inside of the action space 500 may be cool through latent heat and the like. When the atomizer 130 is operated in the heating spray manner, the mist may be supplied to the inside of the action space 500 in a hot state, the leg may be warmed while taking the foot bath, and the inside of the action space 500 may be warmed.

The atomizer 130 may be provided with an ultrasonic spray device and a heating spray device. In this case, since the leg care apparatus is used in more various manners, the user's satisfaction may be improved.

The mist supplied from the atomizer 130 may perform a predetermined action in the action space 500.

For example, the high-temperature mist contacting the user's leg may transfer heat to the user's leg in a conduction manner. The high-temperature mist may be condensed on a surface of the user's leg and then heated by external hot air so that the foot bath is performed by continuously transferring heat to the user's leg in the conduction manner. For another example, the mist condensed on the user's leg may be evaporated to take on the cold fomentation on the user's leg.

The rear surface opening 114 may be closed by the main rear cover 116. The main rear cover 116 may be provided in a shape in which a hole is processed to allow the operation medium to pass therethrough.

The main body outer cover 120 may be provided in a shape that is inclined forward toward an upper side, like the main vertical extension part 111.

Figure 6:
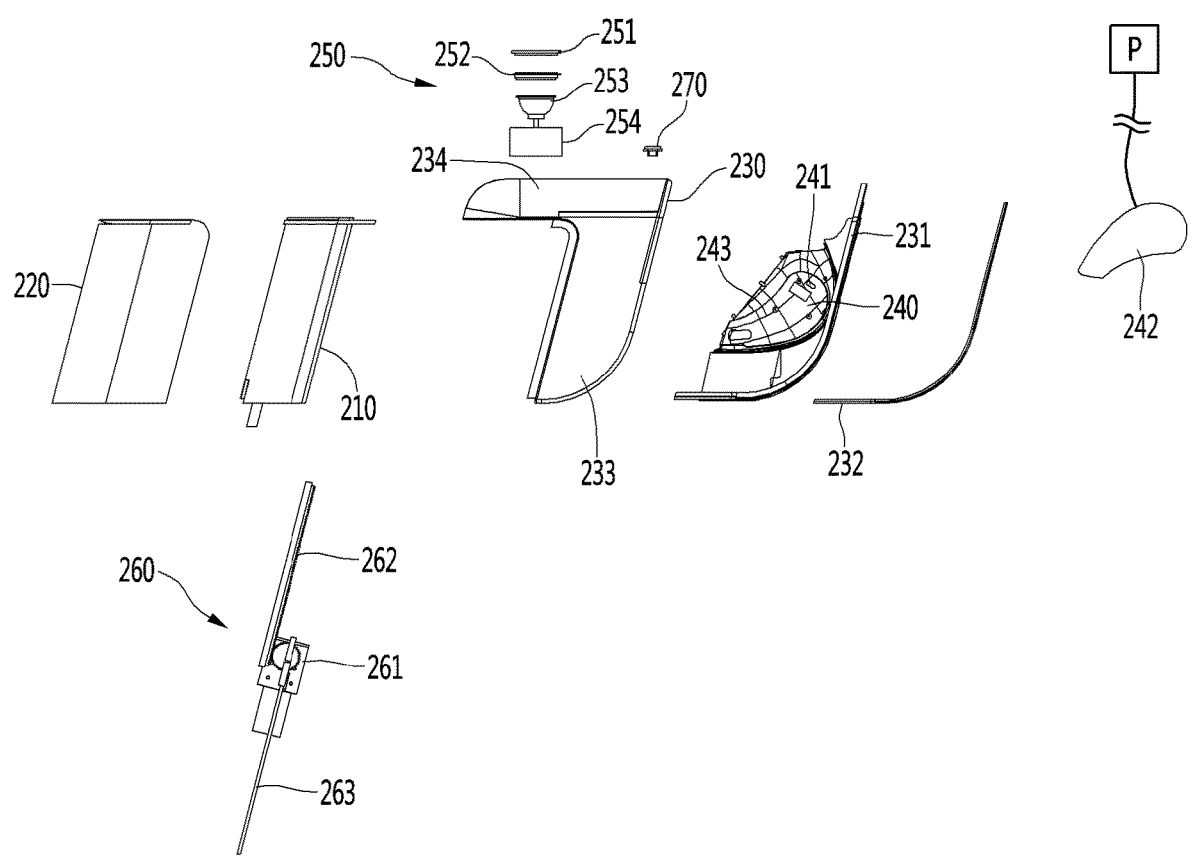
FIG. 6 is an exploded side view of an upper module.

FIG. 6 is an exploded side view of the upper module 200. A configuration and operation of the upper module 200 will be described in more detail with reference to FIGS. 4 and 6.

Referring to FIGS. 4 and 6, the upper module 200 may be moved upward or downward with respect to the main body 100 by the vertical opening device 260. Here, the upper frame 210 may be a component constituting a frame of the upper module 200 and extend to be obliquely inclined forward like the main frame 110.

The vertical opening device 260 may include an elevation driving part 261 including at least a motor, an upper rail 262 extending upward from the elevation driving part 261, and a lower rail 263 extending downward from the elevation driving part 261. The upper rail 262 may be coupled directly or indirectly to the upper frame 210. The lower rail 263 may be coupled directly or indirectly to the main frame 110. At least one of the upper rail 262 or the lower rail 263 may be moved to allow the upper module 200 to ascend or descend.

The upper inner cover 230 and the upper outer cover 220 may be respectively coupled to front and rear portions of the upper frame 210 to define an outer appearance of the leg care apparatus. When the upper frame 210 is moved, the upper inner cover 230 and the upper outer cover 220 may be moved together.

The upper inner cover 230 may include an upper side surface part 233 extending vertically and inclined forward and an upper portion top surface part 234 extending backward from an upper end of the upper side surface part 233 and providing an upper end surface of the leg care apparatus.

The upper portion top surface part 234 may be a surface that is mainly observed when the user uses the leg care apparatus, and thus may be used variously. For example, the upper portion top surface part 234 may be provided with a water supply device 250 that supplies water used in the atomizer 130 and a display 270 that allows the user to control the leg care apparatus.

The water supply device 250 may include a water supply frame 254 in which the supplied water is primarily stored, a water supply supporter 253 that injects water into the water supply frame 254, and a water supply seating panel 252 that supports a water supply cover 251. The user may conveniently supply water by using the water supply device 250.

The display 270 may display information that is necessary for the operation of the leg care apparatus. Manipulation information that is necessary for controlling the leg care apparatus may be inputted by using the display 270. The display 270 may be provided as a touch panel.

The knee care part 240 may be disposed on a front portion of the upper module 200 to care the user's knee. The knee care part 240 may be provided to the knee care frame 231. To allow the knee care frame 231 to be coupled to the upper inner cover 230, a knee care seating panel 232 may be further provided.

The knee care part 240 may include at least one light emitting element 241 that irradiates infrared rays to the knee, at least one massage pad 242 that presses a spaced peripheral portion of patella, and a pump P that controls air pressure to the inside of the massage pad 242. The massage pad 242 may be applied in other methods such as spring pressure control rather than the air pressure control.

The knee care part 240 may include a knee placing part 243. The at least one light emitting element 241 and the at least one massage pad 242 are placed at positions of an inner region of the knee placing part 243, respectively. The knee placing part 243 may be a structure in which a material such as a soft cushion is filled and may apply an overall pressure to the user's knee to care the knee comfortably. According to the knee placing part 243, the action due to the massage pad 242 may be more improved.

Unlike the action space 500, as described above, the knee care part 240 performs an action such as pain relief of the knee by applying pressure and heat.

Figure 7:
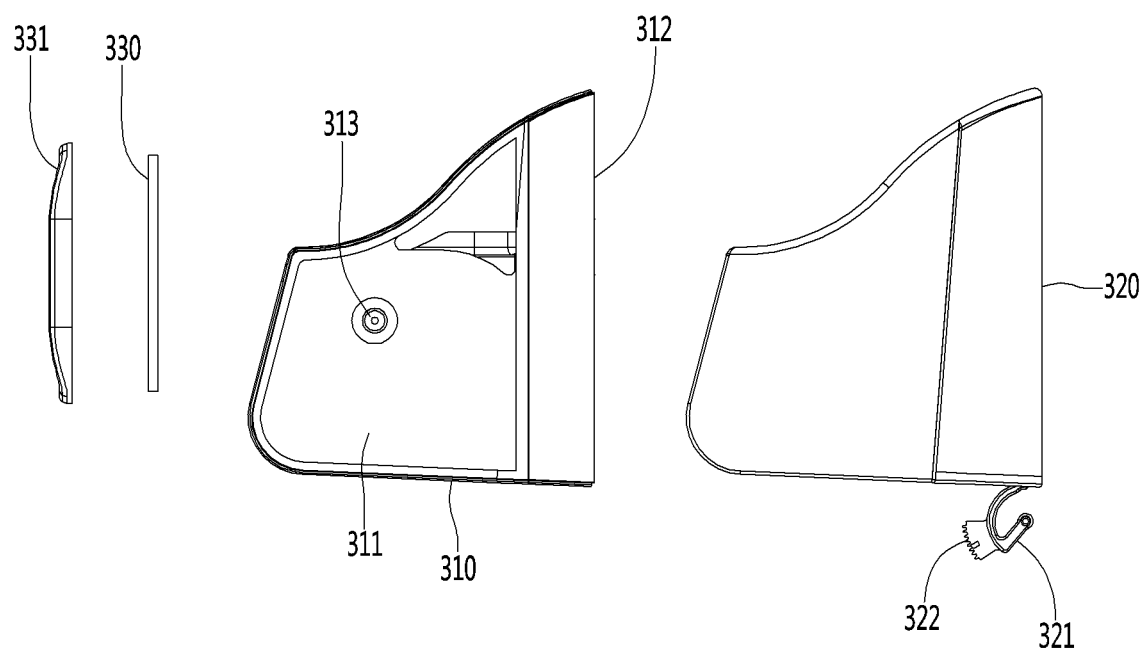
FIG. 7 is an exploded side view of a side module.

FIG. 7 is an exploded side view of the side module 300. A configuration and operation of the side module 300 will be described in more detail with reference to FIGS. 4 and 7.

Referring to FIGS. 4 and 7, the side module 300 rotates backward and forward so that the user may conveniently use the leg care apparatus.

The side module 300 may include a side frame 310 connected to the main frame 110 and a side outer cover 320 provided in front of the side frame 310.

The side frame 310 may include a side portion front surface part 312 and a side portion side surface part 311 extending backward from both sides of the side portion front surface part 312. The side portion side surface part 311 may be provided as two left and right walls, and the main front and rear extension part 112 may be inserted into an inner spaces of the two walls.

A protrusion 313 may be provided inside the side portion side surface part 311, and the protrusion 313 may be guided by the guide slot 115 (see FIG. 5). The positions at which the protrusion 313 and the guide slot 115 are provided may be opposite to each other. However, for stable operation, it is preferable that the protrusion 313 is provided on the side module 300, and the guide slot 115 is provided on the main body 100.

A movement support part 321 supporting the rotation operation of the side module 300 may be provided on a lower portion of a front end of the side outer cover 320. The movement support part 321 may be hung and supported at any point of the bottom module 400 or the main body 100. The movement support part 321 may act as a center point of relative rotation with respect to the main body 100 of the side module 300.

Figure 8:
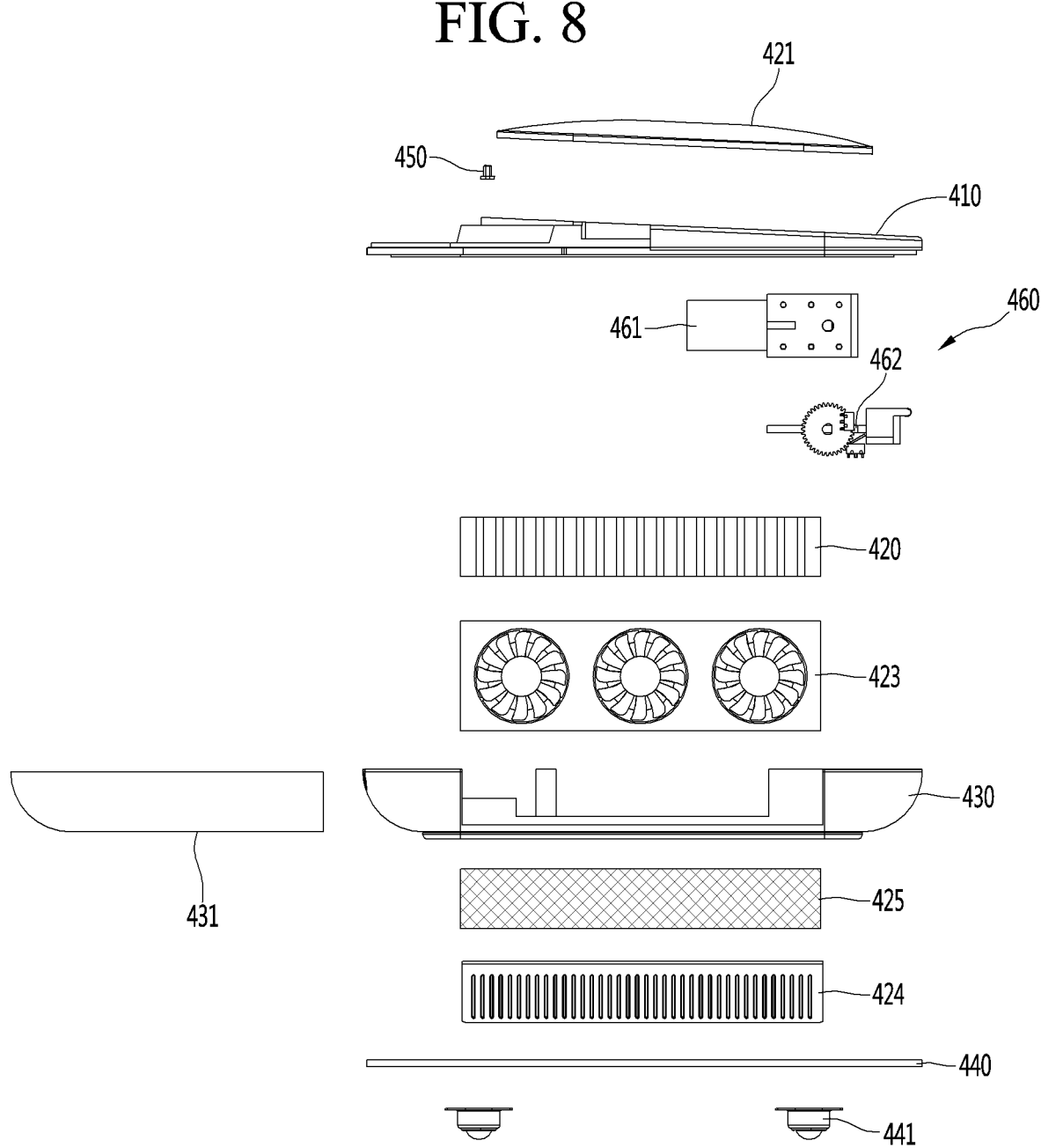
FIG. 8 is an exploded side view of a bottom module.

A movement contact part 322 is provided at an adjacent position of the movement support part 321 to receive driving force of the link driving part 462 (see FIG. 8). For example, the link driving part 462 and the movement contact part 322 may be engaged with each other to receive the driving force of the rotation driving part 461.

An interaction between the main body 100 and the side module 300 may be performed by the rotation operation through the transmission of the driving force of the front and rear opening device 460 and the guiding action of the protrusion 313 and the guide slot 115.

The rotation driving force may be transmitted from the bottom module 400 to the side module 300 by the action connected to the rotation driving part 461, the link driving part 462, and the movement contact part 322 in time series. Here, the side module 300 may rotate in a state of being supported by the movement support part 321.

When the side module 300 is rotated by the rotation driving force, the protrusion 313 of the side module 300 may be guided by being placed inside the guide slot 115. The side module 300 may rotate at a curvature radius by a correct rotation center by the mutual guiding action of the guide slot 115 and the protrusion 313.

A calf thermoelectric module 330 and the calf contact pad 331 may be provided on an inner surface of the side module 300. A thermoelectric element may be provided in the calf thermoelectric module 330 to supply cold and hot air as desired by the user. Accordingly, the foot bath function for the calf portion of the user may be performed.

When the calf thermoelectric module 330 has a large heat load, a separate heat exchange fan may be installed like the foot thermoelectric module 420.

FIG. 8 is an exploded side view of the bottom module 400. A configuration and operation of the bottom module 400 will be described in more detail with reference to FIGS. 4 and 8.

Referring to FIGS. 4 and 8, a plurality of components for the foot bath may be provided in the bottom module 400. The bottom module 400 includes a bottom frame 410, a bottom housing 430 accommodating an outer edge of the bottom frame 410, and a bottom plate 440 that opens and closes a lower portion of the bottom frame 410.

The foot thermoelectric module 420 and the foot contact pad 421 that transfers the cold and hot air of the foot thermoelectric module 420 to the user's foot in a conduction manner may be provided inside the bottom housing 430. The foot thermoelectric module 420 and the foot contact pad 421 may contact each other to transfer heat. The foot contact pad 421 may contact the sole of the user, and the hot or cold air may be transferred to the sole of the foot to perform the foot bath function.

The foot contact pad 421 may be made of a metal having high thermal conductivity, for example, copper or stainless steel so as to uniformly transfer heat to the entire sole of the foot. This may be equally applied to the calf contact pad 331.

When water having a predetermined level is accumulated in the bottom housing 430, the foot contact pad 421 may heat the accumulated water to perform the foot bath function for the foot.

The heat exchange fan 423, the grill 424, and the filter 425 may be further provided as constituents for the hot or cold air that is exhausted from the foot thermoelectric module 420 to the outside. High energy may be supplied to the foot thermoelectric module 420 to supply a large amount of hot or cold air when compared to the calf thermoelectric module 330. Heat generated in and exhausted from the thermoelectric module 420 may be smoothly discharged to the outside by the heat exchange fan 423.

To allow the air circulated to the heat exchange fan 423 to perform a cooling operation without any problem, the grill 424 and the filter 425 may be provided. The air in which foreign substances are filtered by the filter 425 may be supplied to the blower 101 and supplied to the action space 500. In this case, cleaner air may be supplied to the action space 500 to improve the user's satisfaction.

The front and rear opening devices 460 are accommodated in the bottom housing 430 to allow the side module 430 to rotate as described above. A large portion of the front and rear opening device 460 is accommodated in the bottom module 400, but is not limited thereto. For example, the front and rear opening device 460 may be provided to the main body 100.

The bottom housing 430 is provided with a light emitting element 450 that is exposed upward so that heat is irradiated to the user's foot. The light emitting element 450 may perform various functions such as sterilization, ultraviolet light for photocatalytic decomposition, infrared rays, and the like depending on the irradiated light.

The water tray 431 that stores waste water to be discharged and wastes may be further provided at one side of the bottom housing 430. In the water tray 431, water condensed after being atomized by the atomizer 130 may be dropped into and stored. The water tray 431 is provided as a component that is slid to be separated to the outside. A valve may be provided in a flow path through which water flows into the water tray 431 to prevent the water from leaking during the foot bath.

A bottom supporter 441 provided as a wheel or the like is provided on a bottom surface of the bottom plate 440 so that the user may easily move the leg care apparatus. The bottom supporter 441 is provided as a rotatable wheel so that the user conveniently moves and uses the leg care apparatus in various directions. In the case of the elderly, the advantages of the above-described moving device may be largely utilized.

The leg care apparatus according to an embodiment is provided with an atomizer to spray mist into the inside of the action space 500. The mist may cover the user's leg in the action space 500.

The mist that covers the user's leg may be heated by heat transmitted from the outside and may transfer the heat to the user's leg while the user is taking the foot bath. In other cases, the mist that covers the user's leg may be cooled by cold air transferred from the outside or may be evaporated to absorb heat to take the cold fomentation by the absorbed heat.

Hereinafter, a configuration of the atomizer will be described in detail. In the following description, the atomizer and constituents related to the atomizer may be emphasized for ease of understanding.

Figure 9:
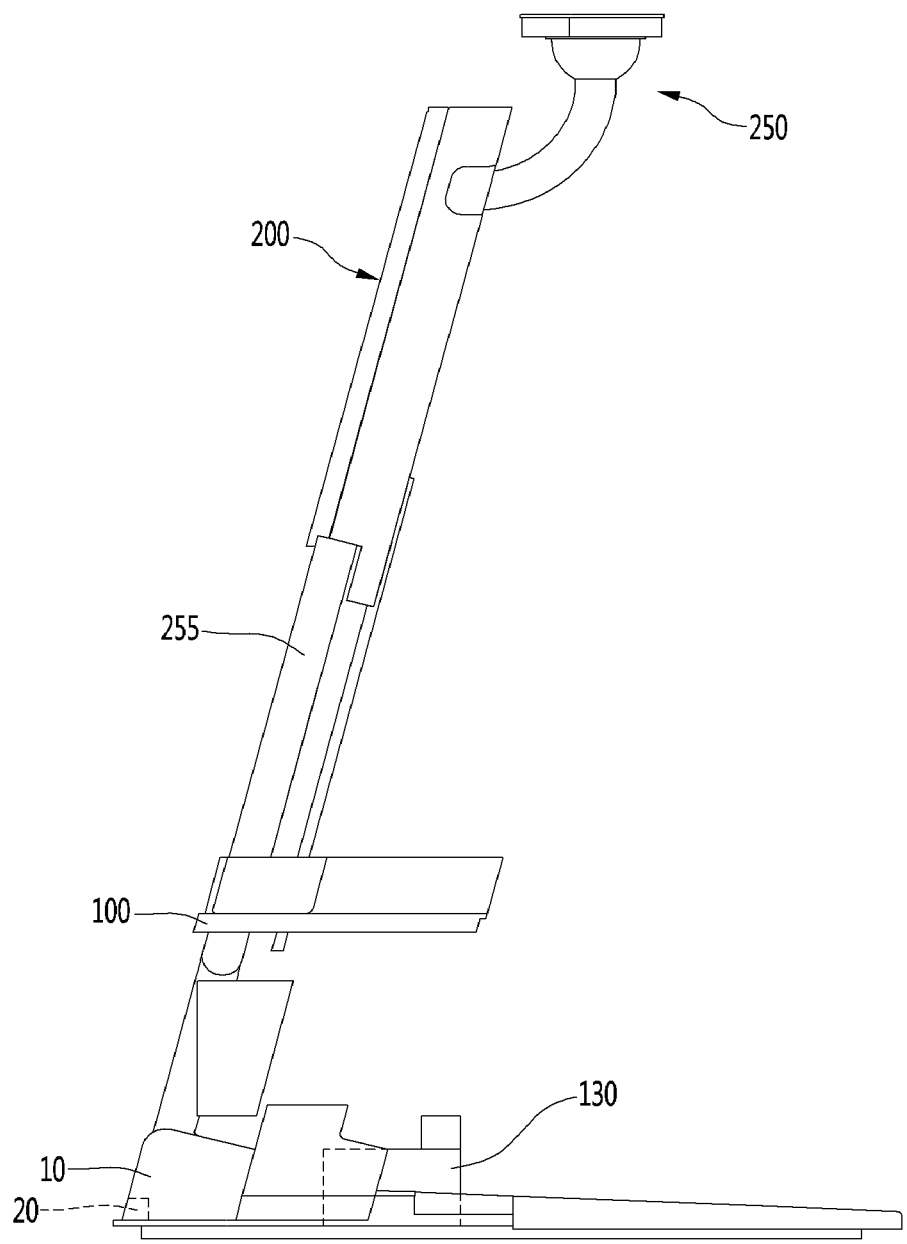
FIG. 9 is a side view of the leg care apparatus that shows constituents related to an atomizer.
Figure 10:
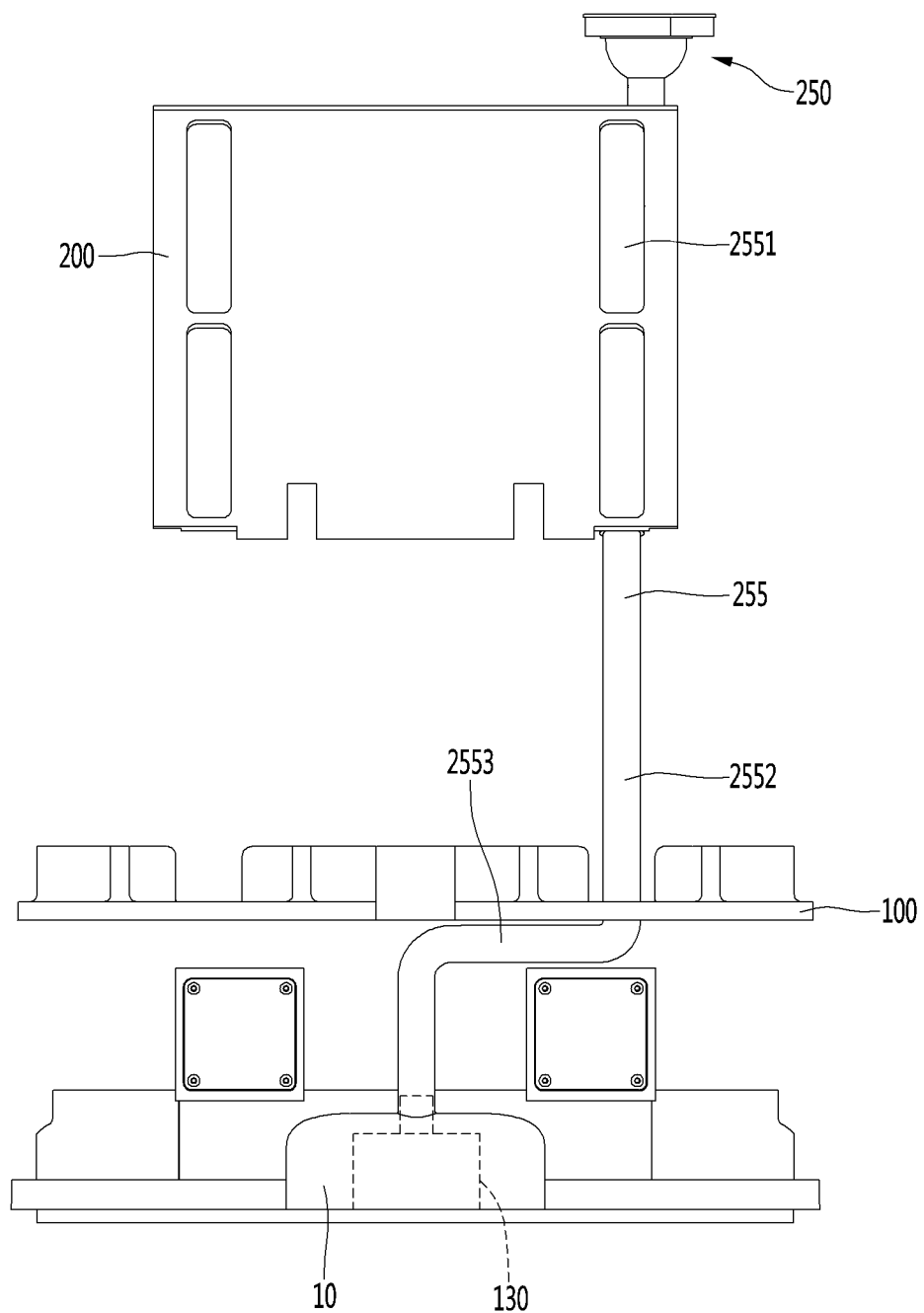
FIG. 10 is a rear view of the leg care apparatus that shows the constituents related to the atomizer.

FIG. 9 is a side view of the leg care apparatus showing constituents related to the atomizer, and FIG. 10 is a rear view of the leg care apparatus showing the constituents related to the atomizer.

Referring to FIGS. 9 and 10, the leg care apparatus according to the embodiment may include an atomizer 130, a water tank 10 that supplies water to the atomizer 130, a water supply device 250 that supplies water to the water tank 10, and a conduct pipe 255 which connects the water supply device 250 to the water tank 10 and through which water passes.

The atomizer 130 is a device that provides mist by applying ultrasonic waves to water. The water tank 10 is configured to secure functional stability of the atomizer 130 by supplying a predetermined amount of water to the atomizer 130. The water supply device 250 is a device in which the user supplies water from the outside. The water supply device 250 is partially exposed through the top surface of the upper module 200 so that the user may conveniently supply water.

The water supply device 250 may be disposed at one side edge of the upper module 200. When the user uses an upper portion top surface part 234 (see FIG. 6) of the upper module 200 as a table, the upper portion top surface part 234 partially exposing the water supply device 250 should not interfere with the user. For example, when the user places an object such as a book on the upper portion top surface part 234, the water supply device 250 may be disposed at one corner of the upper portion top surface part 234 so as not to interfere with the book.

The water supply device 250 may be provided in the upper module 200, and the upper module 200 may be moved vertically with respect to the main body 100. The water supply device 250 is provided at one corner of the upper portion top surface part 234.

To allow the conduct pipe 255 to connect the water supply device 250 to the water storage tank 10, the conduct pipe 255 may be provided in a pipe structure including two pipes that are mutually expandable. For example, the conduct pipe 255 may include a first conduct pipe 2551 connected to one side of the water supply device 250 and a second conduct pipe 2552 connected to one side of the water tank 10.

The other sides of the first conduct pipe 2551 and the second conduct pipe 2552 may overlap with each other by a predetermined length. Even if the first conduct pipe 2551 and the second conduct pipe 2552 are spaced apart from each other in a longitudinal direction, the pipe connection of the first conduct pipe 2551 and the second conduct pipe 2552 may not be disconnected. Even if the upper module 200 is moved upward from the main body 100, the conduct pipe 255 may guide water from the water supply device 250 to the water tank 10 without water leakage.

The conduct pipe 255 may be provided in a form of a corrugated pipe having a stretchable length when not in a configuration in which two pipes overlap with each other. As another configuration, the conduct pipe 225 may be provided as a corrugated pipe having a predetermined length so as to be stretchable, and also be provided as a rigid pipe for coupling by a predetermined length.

At least a portion of each of the first conduct pipe 2551 and the second conduct pipe 2552 may be bent. In the embodiment, the second conduct pipe 2552 may be bent towards a center to provide a conduct pipe bending part 2553. The conduct pipe bending part 2553 is configured to guide water towards the water tank 10 even if the water supply device 250 is provided at one corner of the upper portion top surface part 234. The water tank 10 may be disposed at the center of the main body 100 with respect to the horizontal direction.

The atomizer 130 may be provided in front of the water tank 10. The atomizer 130 may be adjacent to the action space 500 as closely as possible so that the generated mist is directly supplied to the action space 500 without condensation.

The atomizer 130 may be operated using ultrasonic waves. The mist that is in a room-temperature state may be provided using a phenomenon in which water molecules are evaporated from the surface by vibration of the ultrasonic waves.

Figure 11:
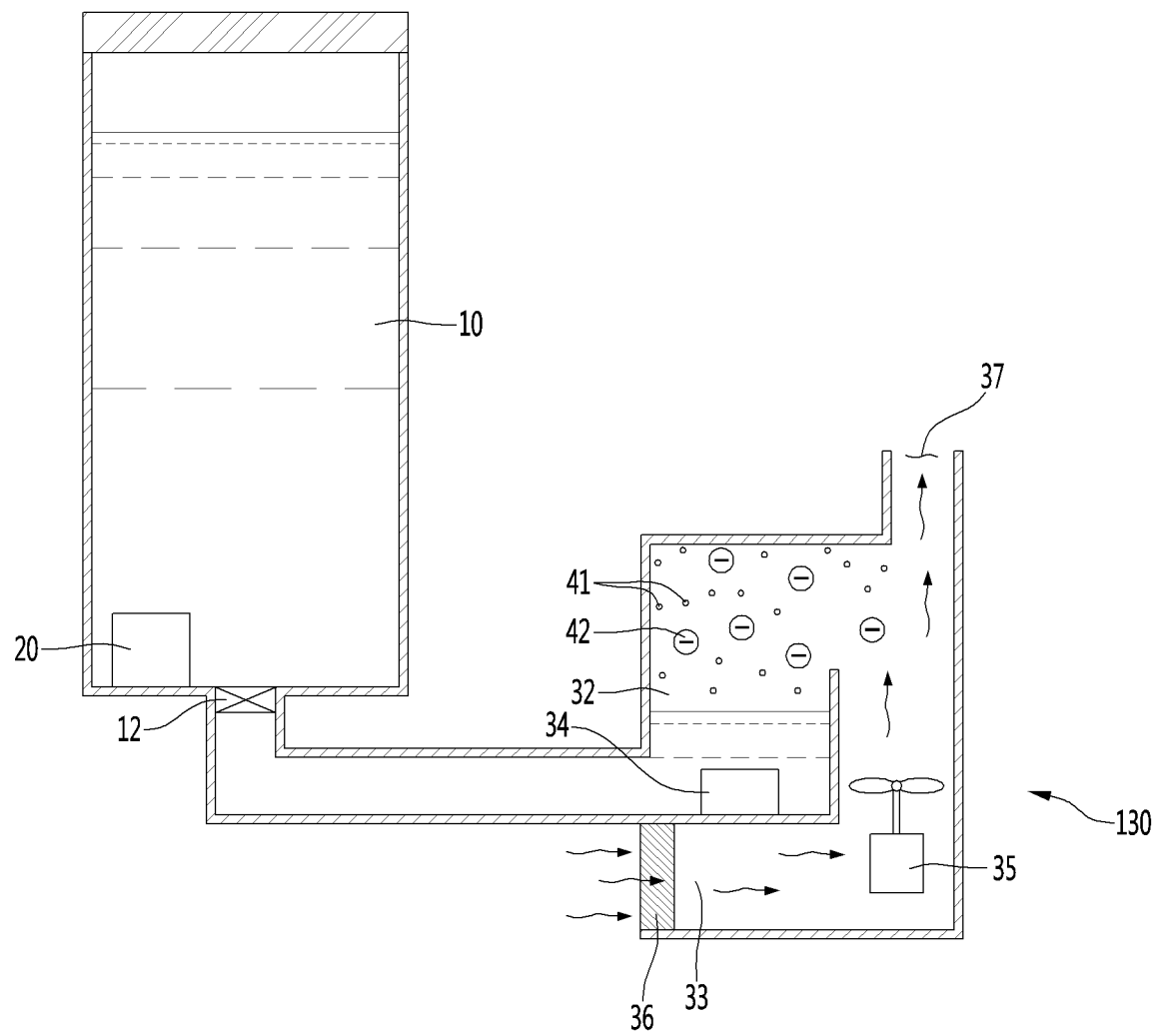
FIG. 11 is a schematic view of the atomizer.

FIG. 11 is a schematic view of the atomizer.

The atomizer 130 may be supplied with water from the water tank 10 to generate fine water particles 41 and anion 42 so as to be sprayed to the outside.

A mist generator 32 having one end coupled to the lower portion of the water tank 10 and the other end coupled to the atomizer 130 is provided. A flow rate control valve 12 is provided at the coupling portion of the water tank 10 and the mist generator 32 to maintain a water level of the mist generator 32 at a predetermined level.

A vibrator 34 may be installed on a bottom surface of the mist generator 32. The vibrator 34 may vibrate the water contained in the mist generator 32 to generate fine water particles 41. Here, a frequency of the vibrator 34 belongs to a region of the ultrasonic wave that is inaudible to the human ear.

A suction hole 33 is defined in one side of the atomizer 130. A spray fan 35 that suctions external air through the suction hole 33 is installed at one side of the mist generator 32. A filter 36 that filters foreign substances contained in the suctioned air may be installed on the suction hole 33. In an embodiment, a prefilter may be installed as a filter for filtering the suctioned air.

It is preferable that a catechin component or an antibacterial component of green tea is applied to the filter 36 to kill bacteria suctioned together with the suctioned air into the filter 36.

A nozzle 37 through which the fine water particles 41 are sprayed to the outside may be installed above the atomizer 130. The nozzle 37 is configured to spray the mist into the action space 500 by loading the mist such as the fine water particles 41 and the anion 42 in the air current blown from the spray fan 35.

A sterilizer that is capable of sterilizing bacteria inhabited in the water stored in the water tank 10 may be provided in the water tank 10. An ultrasonic cell crusher 20 may be installed as the sterilizer.

The mist supplied from the nozzle 37 may be loaded in the strong air current provided by the separate blower 101 to reach every corner of the inside of the action space 500. In addition, the mist supplied from the nozzle 37 may be concentrately supplied to a portion that is adjacent to the nozzle 37 by being loaded in the weak air current provided by the spray fan 35.

The use of the blower 101 may be selected according to various modes of the user's preference and the foot bath. To allow the mist to reach the entire area of the user's leg placed in the action space 500, the blower 101 may be operated.

The foot bath function by the atomizer 130 will be described in more detail.

The mist supplied by the atomizer 130 may cover the user's leg in the action space 500. Thereafter, when the blower 101 provides an air current, the air current may be generated in the action space 500, and the mist that covers the user's leg may be evaporated. The mist may absorb heat from the leg while being evaporated to cool the leg. Thus, the user may enjoy a feeling of being cool.

The cold air of the air current within the action space 500 may be supplied to the user by providing a separate refrigeration cycle to the blower 101 or by providing a thermoelectric module exposed to the blower 101 or the action space 500. In this case, the cool feeling enjoyed by the user may increase even more. The thermoelectric module may include the foot thermoelectric module 420 and/or the calf thermoelectric module 330.

When the blower device 101 provides a hot air current, the air current in the action space 500 may heat the mist that covers the user's leg. The heated mist may heat the legs so that the user enjoys a hot foot bath.

The hot air current of the blower 101 may be achieved by the blower having a separate heater. As another method, the air current within the action space may form a hot atmosphere through a method in which the thermoelectric module is exposed to the action space or the separate heater is provided. The thermoelectric module may include the foot thermoelectric module 420 and/or the calf thermoelectric module 330.

Hereinafter, an embodiment of a high-temperature atomizer that provides high-temperature mist will be described. A related system of the leg care apparatus including the water tank 10 is the same as a room-temperature atomizer of FIGS. 9 to 11. Since the atomizer according to a following embodiment provides high-temperature mist unlike the room-temperature atomizer, the atomizer may be called a high-temperature atomizer.

Figure 12:
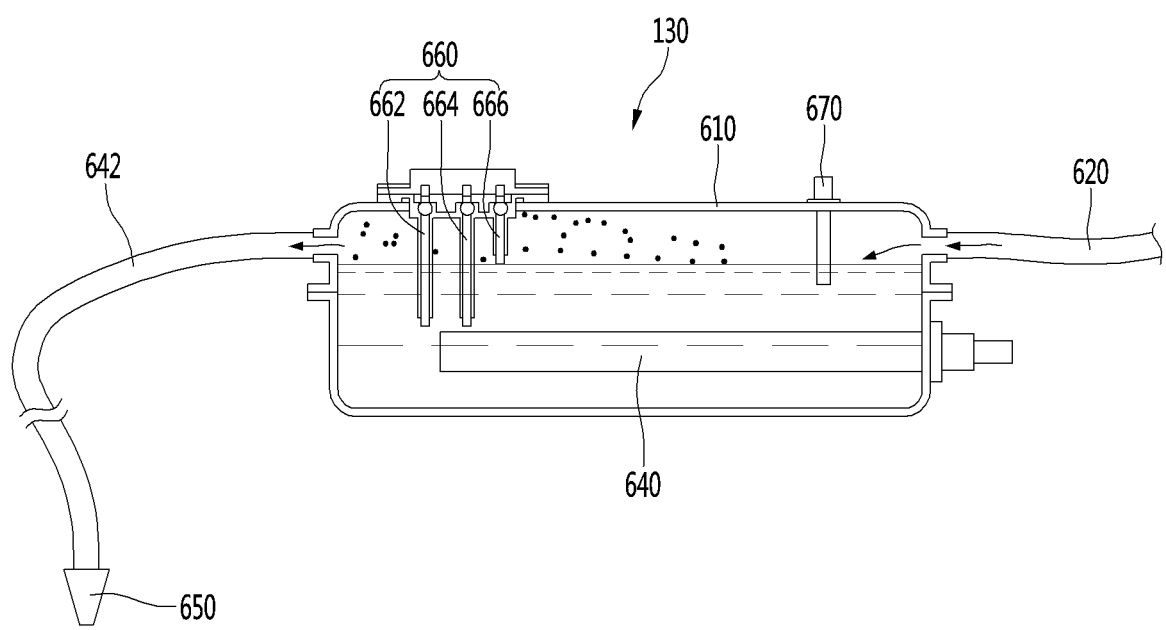
FIG. 12 is a cross-sectional view illustrating an example of the atomizer.

FIG. 12 is a cross-sectional view illustrating an example of the atomizer. Referring to FIG. 12, the atomizer 130 will be described in detail as follows.

Referring to FIG. 12, the atomizer 130 may include a tank 610 in which water is stored, a heater 640 mounted in the tank 610, a water level sensor 660 that measures a water level of the atomizer 130, and a temperature sensor 670 that measures a temperature of the atomizer 130.

The water level sensor 660 may be constituted by a common electrode 662, a low water level electrode 664, and a high water level electrode 666. A high water level and a low water level may be sensed by whether the common electrode 662 and the high water level electrode 666 are electrically connected to each other or whether the common electrode 662 and the low water level sensor 664 are electrically connected to each other.

A water supply hose 620 that supplies water may be connected to one side of the atomizer 130, and a steam supply line 642 that discharges steam in one form of mist may be connected to the other side of the atomizer 130. A nozzle 650 having a predetermined shape may be provided at a front end of the steam supply line 642.

The water supply hose 620 may have one end connected to a water supply part that supplies water to the atomizer, and the nozzle 650 disposed at the front end of the steam supply line 642, i.e., a steam discharge hole may be connected to a predetermined position on the inner surface of the action space 500 to spray the high-temperature mist into the action space 500.

Here, the water supply part may be connected to the water tank 10. A valve may be provided at a connection portion with the water tank 10.

Although the atomizer 130 (hereinafter, for convenience of description, referred to as a "tank heating type") generates mist in a manner in which a predetermined amount of water stored in the tank 610 having a predetermined size is heated by the heater 640 is illustrated and described in the embodiment, the embodiment of the present disclosure is not limited thereto.

That is, in this embodiment, any device capable of generating high-temperature mist may be used as the atomizer. For example, a heater may be installed directly around or inside a predetermined case through which water passes. Accordingly, the water may be heated without being stored in a predetermined tank 610 (hereinafter, for convenience of description, referred to as a "pipe heating type"). In the pipe heating type atomizer, water introduced to flow into the atomizer may be heated and converted into high-temperature mist.

Figure 13:
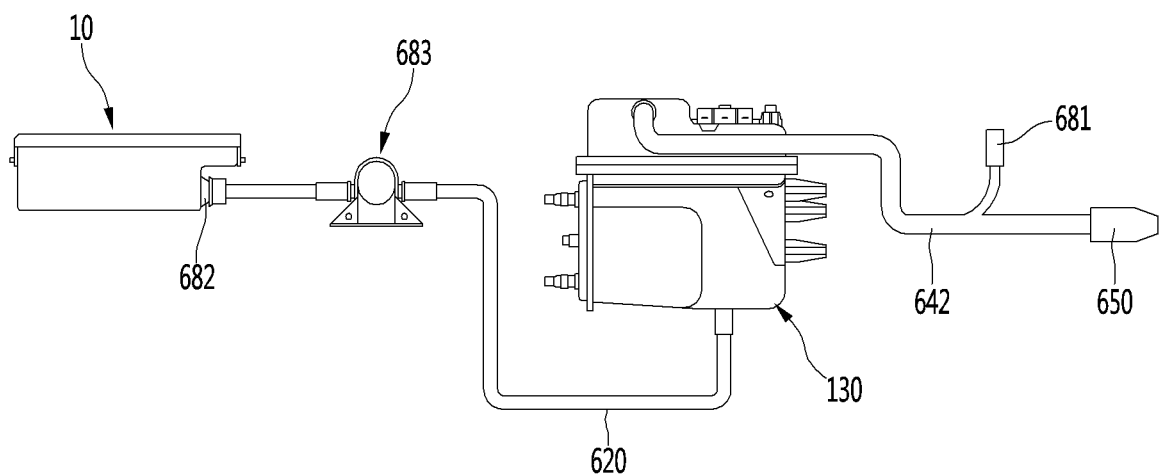
FIG. 13 is a schematic view of a system related to the atomizer.

FIG. 13 is a schematic view of a system related to the atomizer.

Referring to FIG. 13, in this embodiment, the water tank 10 may store a predetermined amount of water as a water supply part that supplies water to the atomizer 130 and may be provided behind the atomizer 130.

A pump 683 may be provided between the water tank 10 and the atomizer 130. The pump 683 may be rotatable forward and backward to supply water to the atomizer 130 or to collect remaining water in the atomizer 130 as necessary. The collection of the residual water as described above is intended to prevent or minimize the accumulation of inorganic matters within the atomizer such as scale. For example, if an amount of inorganic matters contained in the water is small or negligible, a forward-only pump may be used.

The residual water collected into the water tank 10 may be discharged by emptying the water tank 10. Here, the concentration of the inorganic material may be high.

Since the pump 683 that is rotatable forward and backward is used, it may be possible to prevent the failure of the atomizer 130. Specifically, in the high-temperature atomizer used in a manner in which water is boiled to provide mist, after the water is boiled, the inorganic matters remain in the tank 610. The remaining inorganic matters may cause the failure of the atomizer 130. To prevent this failure, when the atomizer is operated for a predetermined time, and the residual water remains by a predetermined level or less, the inorganic matters may be reduced by removing the residual water in the tank 610.

The pump may be replaced with an on/off valve. This may be possible by using a water level difference between the water tank 10 and the atomizer 130. That is, it may be possible to supply water from the water tank 10 to the atomizer 130 by using gravity. In this case, the on/off valve may be turned on to automatically supply the water from the water supply part to the atomizer.

The water may be supplied to a lower portion of the atomizer 130, and the steam may be discharged from an upper portion of the atomizer 130. This may be advantageous for collecting the residual water of the atomizer 130. Of course, as illustrated in FIG. 12, the water may be supplied to an upper portion of the atomizer 130. In this case, a separate drain structure for collecting the residual water may be provided.

A safety valve 681 may be provided in a steam passage that discharges steam from the atomizer 130, i.e., the steam supply line 642. This may be done for preventing a safety accident by preventing a steam pressure from increasing when the steam passage, in particular, the nozzle 650 is blocked.

The foot bath function according to the high-temperature atomizer will be described in more detail.

The high-temperature mist supplied by the atomizer 130 may directly cover the leg of the user, or the high-temperature mist may condense on the leg to perform the foot bath function.

The blower 101 may be additionally operate to allow the high-temperature mist to reach the entire leg area of the user.

When the blower 101 provides a hot air current, the air current in the action space 500 may continuously heat the mist that covers the user's leg. In this case, even when the hot mist is cooled, the foot bath may be continuously performed.

The hot air flow of the blower 101 may be achieved by the blower 101 having a separate heater. As another method, the air current within the action space 500 may form a hot atmosphere through a method in which the thermoelectric module exposed to the action space or the separate heater is provided. The thermoelectric module may include the foot thermoelectric module 420 and/or the calf thermoelectric module 330.

The atomizer of FIGS. 9 to 11 may be a room-temperature atomizer that is operated by ultrasonic waves, and the atomizer of FIGS. 12 and 13 may be a high-temperature atomizer that is operated in a heating manner.

As described above, the room-temperature atomizer or the high-temperature atomizer may be provided separately in the leg care apparatus. The room-temperature atomizer and the high-temperature atomizer may be provided together in the leg care apparatus. Thus, the user may enjoy the foot bath in various ways regardless of a temperature, such as cold or hot fomentation.

Figure 14:
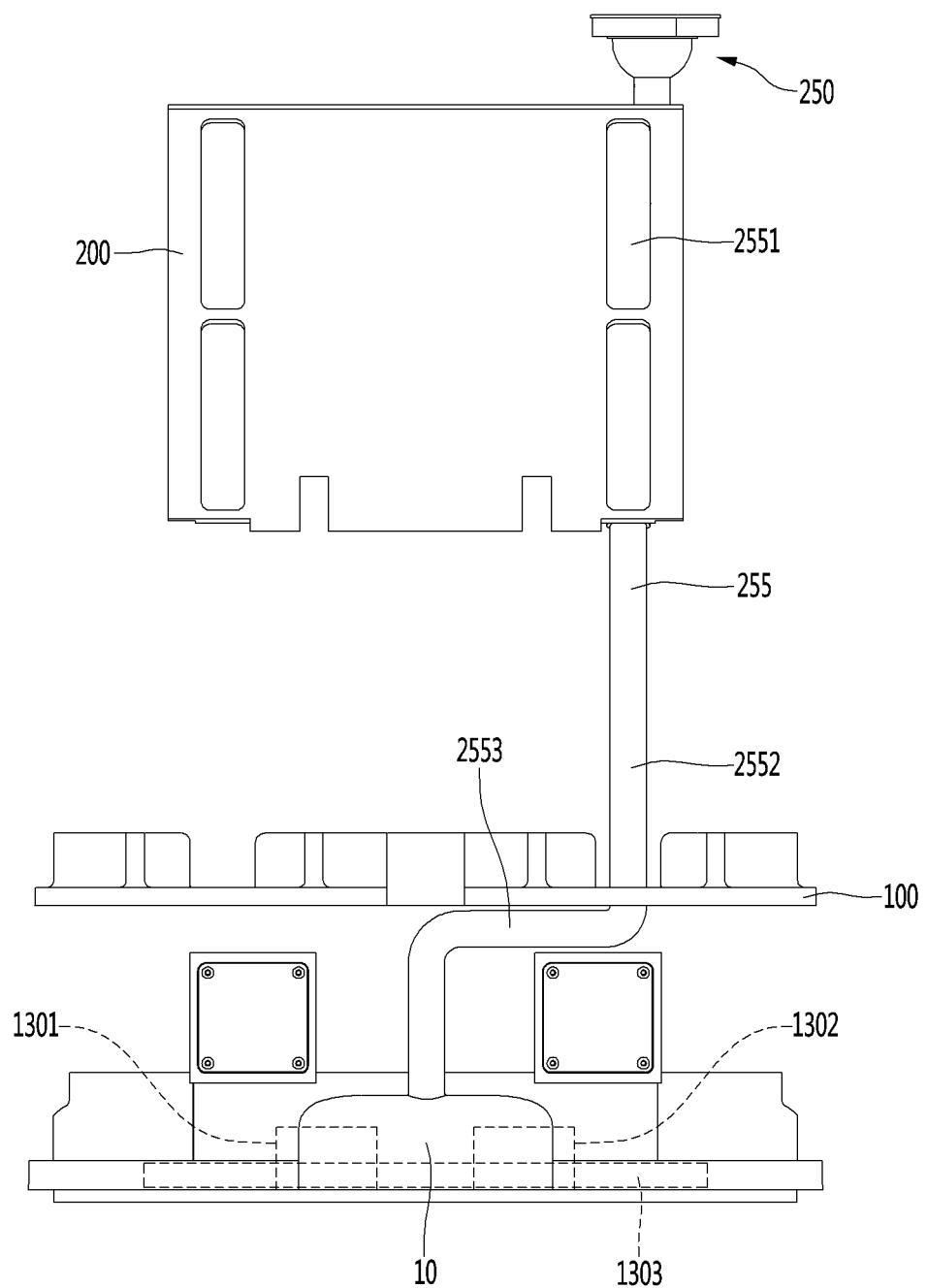
FIG. 14 is a schematic rear view of the leg care apparatus in which a room-temperature atomizer and a high-temperature atomizer are installed together.

FIG. 14 is a schematic rear view of the leg care apparatus in which the room-temperature atomizer and the high-temperature atomizer are installed together. Since other parts are the same in FIG. 14, the already described contents are applied herein, and the description thereof is omitted, and thus, only the parts related to the atomization apparatus will be described.

Referring to FIG. 14, the room-temperature atomizer 1301 capable of providing mist at room temperature and the high-temperature atomizer 1302 capable of providing high-temperature mist may be provided on both sides of the water tank 10.

The mist provided by the room-temperature atomizer 1301 and the high-temperature atomizer 1302 may be widely supplied into the action space 500 so that the mist is evenly distributed on the user's leg surface. For this, a mist supply slit 1303 having a slit structure that is provided lengthily in a left and right direction at the lower portion of the main vertical extension part 111 (see FIG. 5) may be provided.

Since the mist supply slit 1303 is provided lengthily in the left and right direction, the steam may be supplied to both left and right legs of the user. Since the mist supply slit 1303 is provided lengthily, the mist may be prevented from being concentrated and supplied to one portion of the leg. A diffuser may be provided between the nozzles 37 and 650 and the mist supply slit 1303.

Since a discharge hole of the mist supply slit 1303 is provided widely, the mist may be not concentrated to one portion of the leg, and burns due to the high-temperature mist may be prevented. For this, the diffuser and a baffle may be provided between the nozzle 650 and the mist supply slit 1303.

To smoothly supply the mist into the action space 500, the blower 101 may be operated together when the mist is supplied.

Figure 15:
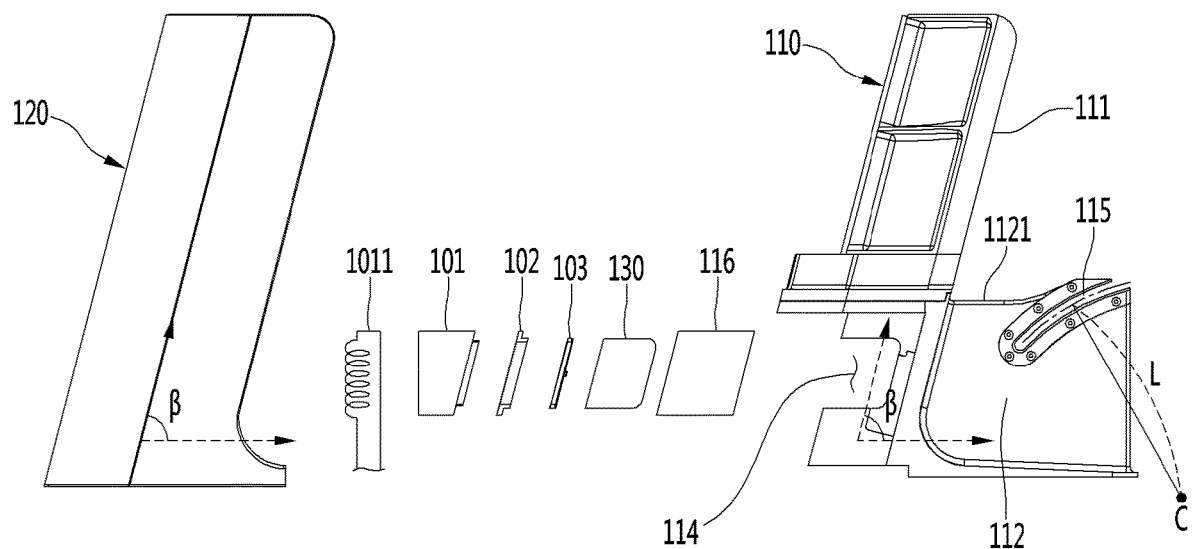
FIG. 15 is an exploded side view illustrating a main body of a leg care apparatus according to another embodiment.

FIG. 15 is an exploded side view illustrating a main body of a leg care apparatus according to another embodiment. Other parts of the leg care apparatus, which are not illustrated in FIG. 5 may be applied to the description of the foregoing embodiment as it is. The description of the original embodiment will be applied to the parts, which are not described, as it is.

Referring to FIG. 15, according to another embodiment, a heating wire 1011 that provides heat to an air current provided by a blower 101 may be further provided. The heating wire 1011 may provide hot air to the action space 500 by loading hot air in the air current when the blower 101 is operated to provide the air current with hot air into the action space 500.

The high-temperature air of the air current may heat the user's legs or the mist inside the action space 500.

The leg care apparatus according to this embodiment may be provide a foot bath atmosphere having a hot atmosphere. A method for controlling the leg care apparatus to perform the foot bath will be described below.

FIG. 16 is a flowchart for explaining a method for controlling a leg care apparatus according to an embodiment.

Referring to FIG. 16, first, mist is provided into an action space 500 (S1). To provide the mist, at least one of a room-temperature atomizer 1301 or a high-temperature atomizer 1302 may be operated.

Various kinds of mist may be provided according to operations of the room-temperature atomizer 1301, the high-temperature atomizer 1302, a heating wire 1011, and a blower 101.

Specifically, when only the room-temperature atomizer 1301 is operated, room-temperature mist may be provided to an action space 500. When only the high-temperature atomizer 1302 is operated, high-temperature mist may be provided to the action space 500. When the room-temperature atomizer 1301 and the high-temperature atomizer 1302 are operated together, a large amount of mist may be provided to the action space 500 at a temperature between room temperature and high temperature.

The operation of the room-temperature atomizer 1301 and the high-temperature atomizer 1302 may be selectively performed in response to a temperature atmosphere and a humidity atmosphere, which are desired by a user. For example, when a large amount of mist is intended to be supplied, the room-temperature atomizer 1301 and the high-temperature atomizer 1302 may be operated together even though the temperature is low. In another example, a case in which only the room-temperature atomizer 1301 is operated may be a case in which the user intends to perform a mist foot bath at room temperature at an operation starting time point.

The mist supplied to the action space 500 may cover the leg of the user to allow the user to enjoy the foot bath (S2).

The mist covering the user's legs may be grown to form water droplets through an aggregation process and a condensation process. As the hot mist newly supplied to the aggregated droplets is aggregated, the aggregated droplets may be maintained at a predetermined temperature.

The aggregated water droplets may fall along the skin of the leg, and droplets may be newly formed by the newly supplied mist so that the user enjoys the foot bath. However, when a large amount of water is accommodated in the action space 500, even if a high-temperature mist is supplied, the amount of heat transferred to the legs may be small. For example, since a heat load inside the action space 500 increases as an amount of water in the action space 500 increases, a temperature of the action space 500 gradually decreases even when the same amount of mist is supplied.

As a result, the temperature inside the action space 500 decreases even if the mist is continuously supplied in the same state. Accordingly, the effects of the foot bath may be deteriorated.

In consideration of the large amount of water stored in the action space, heat may be supplied to the inside of the action space by a part other than mist (S3).

A method for supplying heat into the action space 500 may include, first, operating the blower 101 and the heating wire 1011 to provide a high-temperature air current. Second, operating at least one of the blower 101 or at least one of the thermoelectric modules 330 and 420 so that the heat generated in the thermoelectric module is supplied to the inside of the action space 500 by being loaded in the air current by the blower Third, operating at least one of the blower 101, the heating wire 1011, or the thermoelectric modules 330 and 420 so that an appropriate amount of heat is transferred into the action space 500. Fourth, operating all of the blower 101, the heating wire 1011, and the thermoelectric module 330 and 420 so that the greatest amount of heat is transferred into the action space 500.

The heat supplied in the heat supply process (S3) may sufficiently heat the mist covering the leg so that the user continues to take the foot bath. Alternatively, the supplied heat may directly convection-heat the skin to perform the foot bath. This may be distinguished from the mist that conduction-heats the skin, and thus, the user may enjoy the foot bath by using the conductive heating and convection heating together.

According to a preferred embodiment, when the user intends to take the foot bath at the same temperature while the mist is continuously supplied, the method for supplying the heat may be gradually changed from the method in which relatively low heat is supplied to the method in which relatively high heat is supplied among the above-described four methods. Here, an amount of supplied mist and the heat supplied in the heat supply process (S3) may be compared to select one appropriate method to be performed.

Alternatively, if desired by the user, the user may enjoy the foot bath by selecting the method for supplying the high-temperature heat.

When the mist is heated by other heat supply part other than the mist, the user may continue to enjoy the foot bath by the mist even if there is much moisture in the action space.

According to the method for controlling the leg care apparatus according to an embodiment, the user may perform the foot bath at the same temperature atmosphere regardless of an amount of the mist being continuously supplied.

In the leg care apparatus according to an embodiment, it is possible to perform care on all the leg portions under the thigh. For example, a knee care part 240 may include at least one light emitting element 241 and at least one massage pad 242 to care the knee (see FIG. 6). It is already described that the foot bath is performed by the conduction and the convection even on the calf and the foot.

Thus, the leg care apparatus according to an embodiment may perform various foot bath functions and care functions for the body through various heating devices. Particularly, the user may perform the foot bath through all methods of radiation, conduction, and convection, which are capable of being expected in the foot bath. In this case, it is possible to provide the best function for the user who wants the hot fomentation.

Hereinafter, an effect of the leg care apparatus corresponding to the foot bath function of the strong hot fomentation will be described. The function of the strong hot fomentation may be applied more preferably in the case of the elderly.

First, a configuration of the knee care part 240 will be described.

Figure 17:
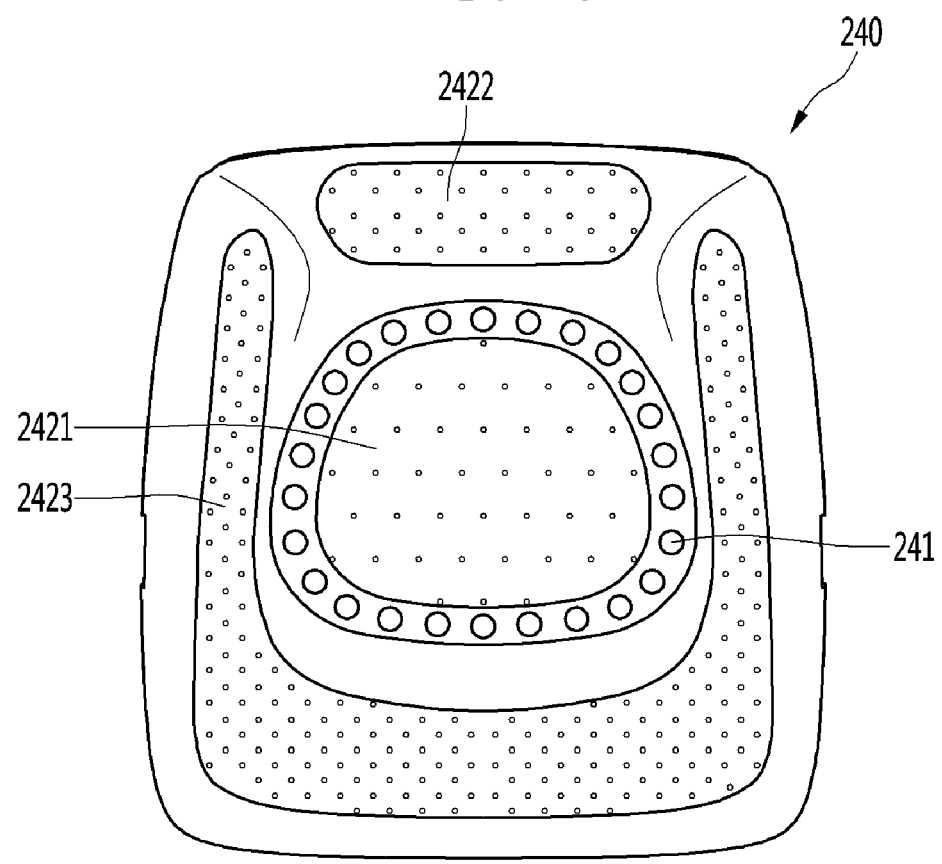
FIG. 17 is a view illustrating a configuration of a knee care part.

FIG. 17 is a view illustrating a configuration of the knee care part.

Referring to FIG. 17, the knee care part 240 includes at least one light emitting element 241 that irradiates infrared rays to the knee and applies heat, and at least one massage pad 242 that performs massage by pressing the periphery of the patella. The massage pad 242 may massage the knee through pressing and relaxation. The light emitting element 241 and the massage pad 242 may be attached to an inner surface of the knee care part 240.

Specifically, the massage pad 242 may include a central massage pad 2421 for massaging a portion below patella femoris, an upper massage pad 2422 disposed above the central message pad 2421, and a circumferential massage pad 2423 for massaging the peripheral portion of the patella except for the upper side. The massage pad 242 may relieve knee pain through continuous pressing and relaxation.

A plurality of light emitting elements 241 surrounds the peripheral portion of the central massage pad 2421. The light emitting element 241 may care the knee by irradiating a radiant heating source such as the infrared rays. the user may expect pain reduction and pain relief effects of the knee through the knee care part 240. The heat generated from the light emitting element 241 may be heated by directly heating the user's knee and also may provide radiant heat to the action space 500.

A method for controlling the leg care apparatus according to an embodiment, which performs the foot bath for the strong hot fomentation will be described.

Figure 18:
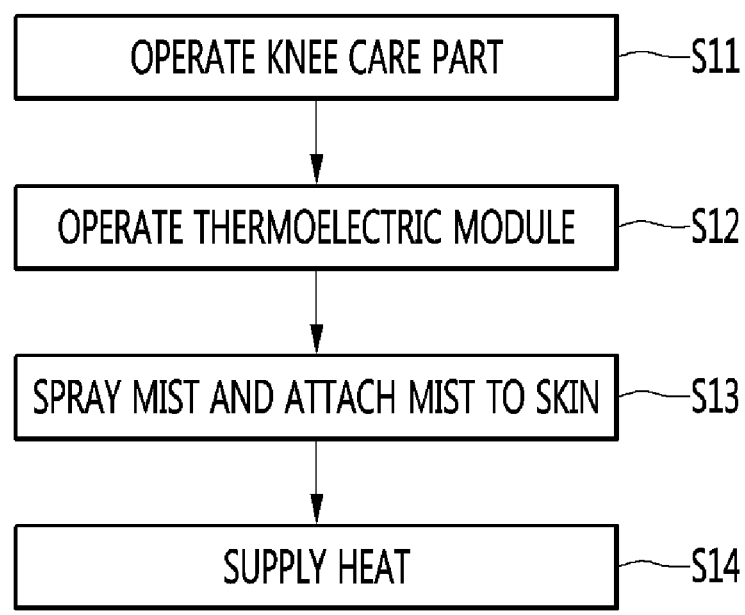
FIG. 18 is a flowchart for explaining a method for controlling a leg care apparatus according to another embodiment.

FIG. 18 is a flowchart for explaining a method for controlling a leg care apparatus according to another embodiment.

Referring to FIG. 18, a knee care part 240 is operated (S11). Here, a light emitting element 241 may be operated to apply radiant heat by infrared rays to the inside of an action space 500. A knee care part 240 may not only care the user's knee inserted into the action space 500, but also radiantly heat an inner space of the action space 500 directly when the user's feet are not inserted into the action space 500.

At least one of the thermoelectric modules 330 and 420 may be operated after the knee care part 240 is operated or may be operated together with the knee care part 240 (S12). As the thermoelectric module is operated, it is possible to care the user's feet and calf inserted into the action space 500. In a state in which the user's leg is not inserted into the action space 500, the thermoelectric modules may directly transfer conductive and convective heat to an inner space of the action space 500. Alternatively, it may also transfer low radiant heat, but since the temperature is not high, the amount of heat may be significantly less than the conductive and convective heat.

The knee care part 240 and the thermoelectric modules 33 and 420 may provide heat to the action space 500 more quickly than other heating parts.

The knee care part 240 and the thermoelectric modules 330 and 420 may be operated to maintain a high-temperature atmosphere having a predetermined temperature or more inside the action space 500. Here, mist may be sprayed through the atomizer 130 (S13). Since the mist is in a state of receiving energy in the high-temperature action space, when covering the user's leg, the user's leg may be more quickly foot bathed.

The user may insert their leg into the action space 500 while the knee care part 240 and the thermoelectric modules 330 and 420 are operated. In this case, since the leg is inserted into the preheated action space, the foot bath function may be more quickly performed. In the case in which the mist is sprayed in advance, since the mist leaks to the outside, it is not preferable to be operated before the user's leg is inserted into the action space 500. This may be equally applied to the case of the blower 101.

Thereafter, as described above, at least one of a heating tool including a heating wire 1011 and the blower 101 may be operated to maintain the high-temperature mist. The mist may be maintained at a higher temperature. Here, the hot air current may contact the skin of the leg so that condensed water droplets are heated.

According to this embodiment, the user of which their leg is inserted into the action space 500 may quickly start the foot bath in a hot atmosphere. According to this embodiment, the user may implement the foot bath function according to strong hot fomentation.

In the leg care apparatus according to an embodiment, a bottom plate 440 provided on the lowermost side of the apparatus, and a bottom supporter 441 provided on a bottom surface of the bottom plate 440 has been described (see FIG. 8). The bottom supporter 441 may include a wheel as an example. Furthermore, the wheel may be rotatable, and thus be easily moved and changed in direction.

Hereinafter, a portion related to the bottom plate 440 and the bottom supporter 441 will be described in detail.

Figure 19:
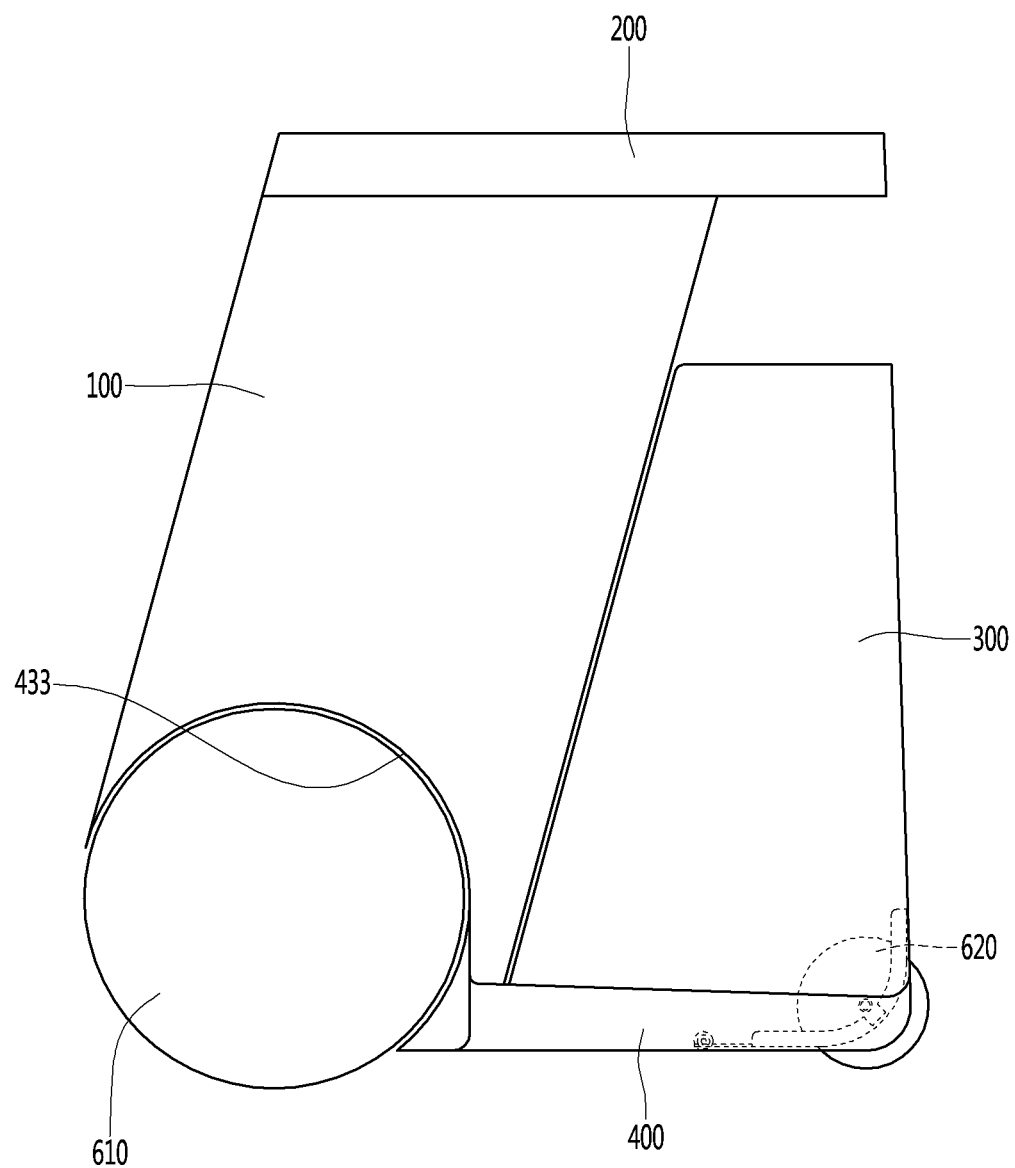
FIG. 19 is a side view of a leg care apparatus so as to emphasize a wheel according to another embodiment.
Figure 20:
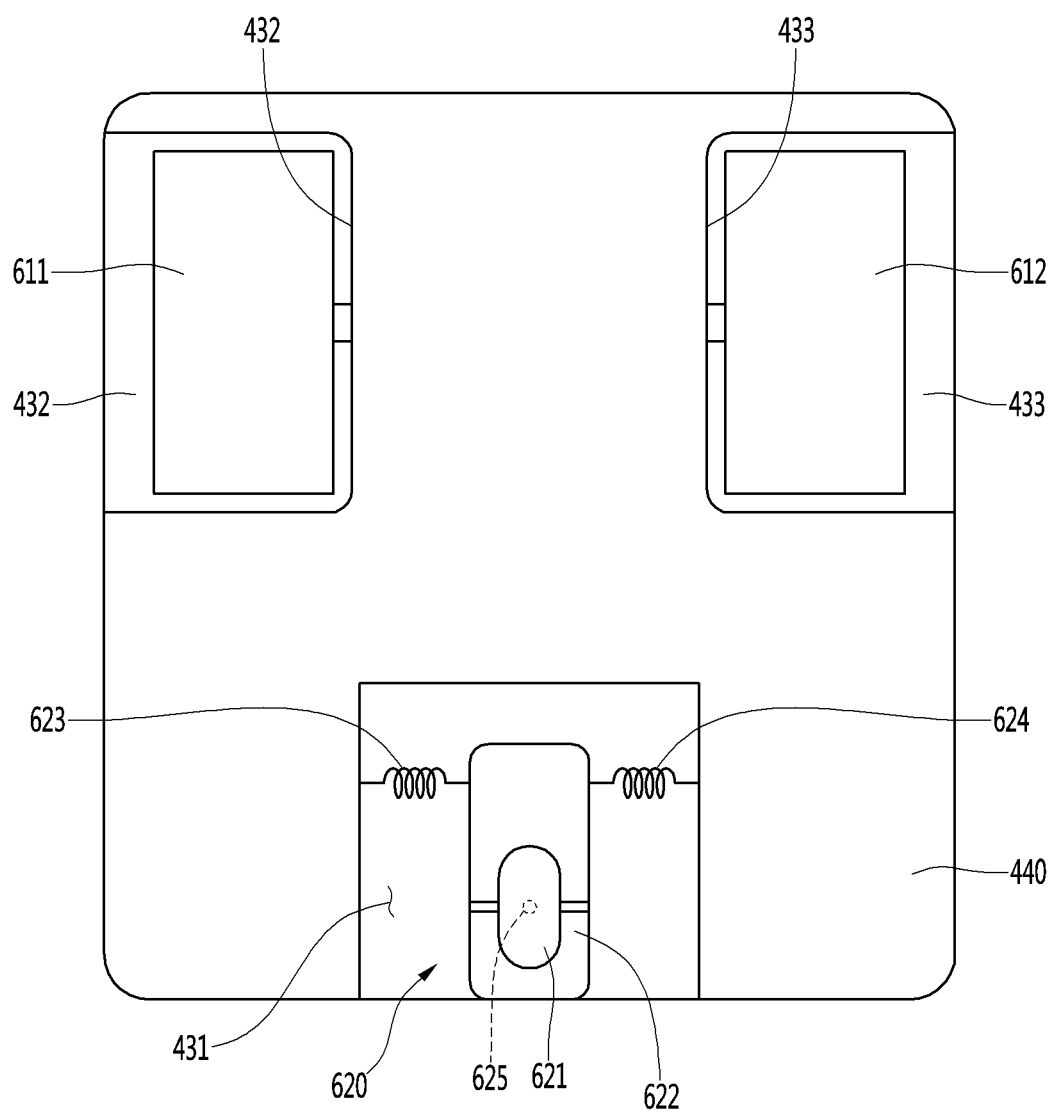
FIG. 20 is a bottom view of a leg care apparatus according to another embodiment.

FIG. 19 is a side view of a leg care apparatus so as to emphasize a wheel according to another embodiment, and FIG. 20 is a bottom view of a leg care apparatus according to another embodiment. FIGS. 19 and 20 are schematically illustrated for convenience of comprehension.

Referring to FIGS. 19 and 20, three wheels may be placed on a bottom surface of a bottom module 400. For example, a large wheel 610 may be placed at a rear portion of the bottom module 400, and a small movable wheel 620 may be placed at a front portion of the bottom module 400.

The large wheel 610 includes two large wheels 611 and 612 at rear left and right portions of the bottom module 400. Each of the large wheels 611 and 612 may be provided as a wheel having a large diameter to support a self-weight of the leg care apparatus.

The movable wheel 620 may also perform a function of supporting the self-weight, but may be provided as a wheel having a small diameter so as to easily and freely change in direction as a main function. The movable wheel 620 may be freely rotated. The moving direction of the leg care apparatus may be conveniently adjusted by controlling the leg care apparatus through force applied by the user in a front and rear direction and a left and right direction. The movable wheel 620 may be provided at a center with respect to the left and right sides, and thus may be easily changed in direction.

The movable wheel 620 may be provided one by one on the left and right sides. In this case, the user may have difficulty in controlling the rotation angles of the two movable wheels together. However, since the load is evenly distributed between the two movable wheels, there is an advantage that durability of the movable wheels is improved.

The large wheels 611 and 612 may be partially accommodated in second and third accommodation grooves 432 and 433 at the rear left and right portions of the bottom plate 440 and the bottom housing 430. At least a portion of the large wheels 611 and 612 may protrude to the outside of the accommodation grooves 432 and 433, and the protruding portions may contact the bottom surface. A central axis of the large wheel may be supported by the bottom housing 430, and thus, the large wheel may rotate. As the large wheel rotates, the leg care apparatus may be smoothly moved.

A portion of the movable wheel 620 may be accommodated in the first accommodation groove 431 recessed from a front central portion of the bottom plate 440 and the bottom housing 430. The first accommodation groove 431 may have a predetermined distance between the first accommodation groove 431 and the movable wheel 620 to accommodate the movable wheel 620 that is moved horizontally. For example, to prevent the movable wheel 620 from contacting an inner surface of the first accommodating groove 431 even if the movable wheel 620 is moved horizontally, the first accommodating groove 431 is larger than a maximum rotation range of the movable wheel 620. In the drawing, the left and right width of the first accommodation groove 431 are about three times as large as the movable wheel 620.

The movable wheel 620 may include a wheel 621 and a wheel housing 622 supporting the wheel 621. The central axis of the wheel 621 is supported by the wheel housing 622, and the wheel 621 may be rotated by the central axis with respect to the wheel housing 622.

Both ends of a rotation support shaft 625 may be connected to the bottom housing 430 and the wheel housing 622 so that the wheel housing 622 rotates with respect to the first accommodation groove 431. At least one end of both the ends of the rotation support shaft 625 may be rotatable. Both the ends of the rotation support shaft 625 may be fixed to the bottom housing 430 and the wheel housing 622 to support a load from an upper side.

The wheel housing 622 may rotate about a rotation center shaft 625, and the movement of the wheel housing 622 may be limited in the first accommodating groove 341. A rotation angle of the wheel housing 622 may be controlled according to force applied by the user. As a result, the moving direction of the leg care apparatus may be changed by the force applied by the user.

Even if the wheel housing 622 rotates about the rotation support shaft 625 by an external force, when the external force is lost, the rotation angle in a linear direction may be maintained. Here, the straight direction may refer to the front and rear direction with respect to the user. That is to say, when the user wants to move the leg care apparatus only forward and backward and where the external force applied in the left and right direction is either small or none, it is preferably moved only forward and backward.

As described above, to give priority to the movement in the front and rear direction of the leg care apparatus, posture adjustment parts 623 and 624 may be provided. The posture adjustment parts 623 and 624 may be achieved by an elastic member connecting the wheel housing 622 to the bottom housing 430 in the left and right direction. The posture adjustment parts 623 and 624 extend horizontally in the first accommodation groove 431 to connect a rear portion of the wheel housing 622 to the bottom housing 430.

When the wheel housing 622 rotates in the direction in which the posture adjusting parts 623 and 624 are stretched, the posture adjustment parts 623 and 624 may apply contraction force to allow the wheel housing 622 to return to its original position. On the contrary, when the wheel housing 622 rotates in the direction in which the posture adjusting parts 623 and 624 are contracted, the posture adjustment parts 623 and 624 may apply stretching force to allow the wheel housing 622 to return to its original position. Alternatively, in the case of the structure capable of applying both the contracting force and the stretching force according to the manner of the posture adjustment part, only one posture adjustment part may be provided.

Figure 21:
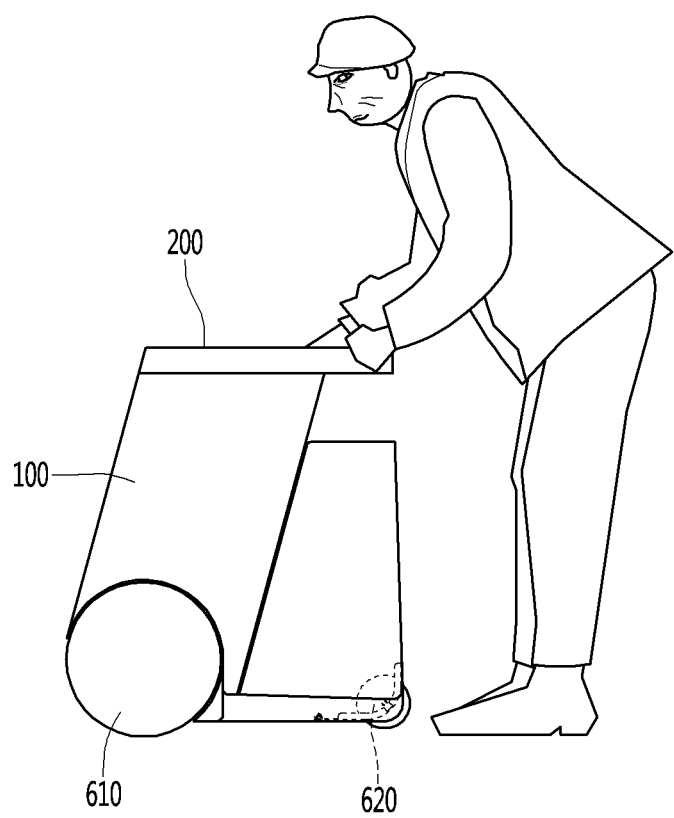
FIG. 21 is a view illustrating a state in which a user holds and moves the leg care apparatus.

FIG. 21 is a view illustrating a state in which the user holds and moves the leg care apparatus.

Referring to FIG. 21, the user may hold an upper portion of the leg care apparatus at the front side to push or pull the upper portion, thereby moving the leg care apparatus.

When the user applies the pushing force forward and backward, the movable wheel 620 is aligned in the front and rear direction, which is an original installation angle, and thus, the leg care apparatus may only move forward and backward. When the user applies force in the front and rear direction and the left and right direction, the movable wheel 620 may rotate and then be moved about the rotation support shaft 625.

The force applied by the user in the left and right direction may be directly transmitted to one movable wheel 620 provided in the front center of the leg care apparatus to which the user applies the force. Therefore, the rotation of the movable wheel 620 may be smoothly controlled. In addition, since the force applied by the user is transmitted directly to the movable wheel 620, the rotation of the movable wheel may be more smoothly controlled.

When the movable wheel 620 is provided at the rear side of the bottom module 400, since the force applied by the user is obliquely inclined to be transmitted to the rear side, the rotation of the movable wheel 620 may not be smoothly controlled.

When the direction change of the leg care apparatus is completed, and the user disengages the force applied to the left and right, and the movable wheel 620 may return to the installation angle to be aligned in the front and rear direction. In this case, restoring force of the elastic member, which is the restoring force of the posture adjustment parts 623 and 624, may be applied.

Due to the configuration and operation as described above, the leg care apparatus may be conveniently pushed or pulled by the user so as to be moved.

Another embodiment included in the spirit of the present disclosure is further described.

One of the upper module and the side module may not be provided. Thus, only one of the upper module and the side module may be opened so that the user inserts their leg into an action space. In this case, there is a limitation in that the user's inconvenience slightly increases, but the operation and action of the leg care apparatus is not impossible. Nevertheless, the embodiment in which both the upper module and the side module are provided is most preferable for the convenience of the user.

One of the foot contact pad and the calf contact pad may not be provided. Thus, even if only one contact pad is used, heat and cold air may be transferred to the user's legs by the other heat transfer part. In this case, there is a limitation in that the user's inconvenience slightly increases, but the operation and action of the leg care apparatus is not impossible. Nevertheless, the embodiment in which both the leg contact pad and the calf contact pad are provided is most preferable for the convenience of the user.

Although the atomizer is described as being provided to the bottom module, the embodiment is not limited thereto, and the atomizer may be provided below or above the main body.

The foot bath due to conductive heating by the mist and thermoelectric module, and the foot bath due to convection heating by the blower may be selectively performed to perform the foot bath.

According to the present disclosure, even the elderly may conveniently care their leg thereof by using the foot bath. In particular, since the handling difficulties caused when using a lot of water is eliminated, even people with limited mobility may use the leg care apparatus conveniently.

In particular, the elderly who suffer from orthopedic diseases may reduce the pain without relying on drugs and may perform the minimum movement that is necessary for the operation of the apparatus.

According to the present disclosure, since the foot bath is enjoyed using the room-temperature mist and the high-temperature mist, the user may enjoy the foot bath more conveniently in various modes. According to the present disclosure, the foot bath may be enjoyed regardless of the amount of mist continuously supplied.

According to the present disclosure, the elderly may be use the leg care apparatus while moving the leg care apparatus more conveniently.

According to the embodiment, the user may adjust the size and the like of the leg care apparatus to be suitable for his/her own body and conveniently operate the leg care apparatus.

According to the embodiment, since the leg car apparatus is safely used even in the high humidity environment, the risks of burns and electric shock may be reduced.

According to the embodiment, the use may conveniently move the leg care apparatus, and the leg care apparatus may be conveniently used in a narrow indoor space due to the compact size thereof.

According to the embodiment, the leg care apparatus may include a firm frame so as to be used for a very long time without being damaged.

According to the embodiment, since the heat atmosphere of the heating element is transmitted to the feet in the various manners such as conduction, convection, and radiation, the foot bath effect may be improved, and the user's satisfaction may increase.

According to the embodiment, since the hot and cold air are directly transferred to the portion at which the hot and cold air are required, the more improved foot bath effect may be obtained, and the energy consumption may be saved.

According to the embodiment, the mist sprayed into the foot bath space may be heated indirectly in the state of contacting the user's leg to take the hot fomentation, and the cold fomentation may be taken by using the absorption heat while the mist is evaporated.

According to the embodiment, since the foot bath is performed using the conductive heating manner and the convection heating manner, the user that has the foot bath may obtain greater satisfaction.

According to the embodiment, since the leg care apparatus is moved while conveniently pushed and changed in direction, the user may conveniently handle the leg care apparatus. Particularly, the elderly may also conveniently move the leg care apparatus.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement which are within the scope of the disclosure, the drawings and the appended claims. In addition to variations and modifications in the component parts and/or arrangements, alternative uses will also be apparent to those skilled in the art and are within the scope of the claims.

What is claimed is:

1. A leg care apparatus comprising:
   a main body configured to provide an action space to accommodate a leg;
   a bottom module disposed at a bottom surface of the main body and in which a component for a foot bath is accommodated; and
   an action space adjustment module configured to adjust a size of the action space,
   wherein the action space adjustment module comprises a side module in which at least a portion of a front surface of the action space is defined and which opens and closes an inlet through which the leg is inserted into the action space.

2. The leg care apparatus according to claim 1, wherein the action space adjustment module comprises an upper module in which at least a portion of a top surface of the action space is defined and which opens and closes an inlet through which the leg is inserted into the action space.

3. The leg care apparatus according to claim 2, wherein the upper module is slidable vertically with respect to the main body.

4. The leg care apparatus according to claim 2, further comprising a knee care part configured to care a user's knee disposed at the upper module.

5. The leg care apparatus according to claim 1, wherein the side module is rotatable with respect to the main body.

6. The leg care apparatus according to claim 5, wherein the side module is supported by the bottom module.

7. The leg care apparatus according to claim 1, further comprising a contact pad configured to conduct and transfer a temperature atmosphere by contacting a user's body disposed at at least one of the main body, the action space adjustment module, and the bottom module.

8. The leg care apparatus according to claim 1, further comprising an atomizer configured to provide mist into the action space.

9. The leg care apparatus according to claim 8, wherein the atomizer comprises at least one of an ultrasonic spray device and a heating spray device.

10. The leg care apparatus according to claim 1, further comprising a bottom supporter configured to allow movement of the leg care apparatus.

11. The leg care apparatus according to claim 10, wherein the bottom supporter includes two kinds of wheels having at least different sizes.

12. The leg care apparatus according to claim 11, wherein a large wheel having a relatively large size among the two kinds of wheels is installed at a rear portion of the bottom module.

13. The leg care apparatus according to claim 12, wherein the large wheel is placed on each of both left and right sides of the bottom module.

14. A leg care apparatus comprising:
a main body configured to provide an action space to accommodate a leg;
a bottom module disposed at a bottom surface of the main body; and
at least one of an upper module movably coupled to an upper portion of the main body and a side module movably coupled to a front portion of the main body so as to adjust an inlet, through which the leg is inserted.

15. A leg care apparatus comprising:
a main body configured to provide an action space to accommodate a leg;
a bottom module disposed below the main body to support the main body; and
a bottom supporter configured to allow movement of the leg care apparatus,
wherein the bottom supporter includes two kinds of wheels having at least different sizes wherein a movable wheel having a relatively small size among the two kinds of wheels is installed at a front portion of the bottom module and is rotatable,
wherein a user holding portion of the leg care apparatus is more adjacent to the movable wheel than the other of the two kinds of wheels.

16. The leg care apparatus according to claim 15, wherein the movable wheel comprises:
a wheel;
a wheel housing configured to support the wheel; and
a rotation support shaft configured to vertically connect the wheel housing to the bottom module, the rotation support shaft being configured to allow rotation of the wheel housing in a left and right direction.

17. The leg care apparatus according to claim 16, further comprising an elastic member configured to connect the wheel housing to the bottom module, the elastic member being configured to provide restoring force by which the wheel housing returns to an installation angle.

\* \* \* \* \*